United States Patent [19]

Schnorrenberg et al.

[11] Patent Number: 5,700,827
[45] Date of Patent: Dec. 23, 1997

[54] AMINO ACID DERIVATIVES, PROCESSES FOR THE MANUFACTURE THEREOF AND PHARMACEUTICAL COMPOSITIONS (II) CONTAINING THESE COMPOUNDS

[75] Inventors: Gerd Schnorrenberg, Gau-Algesheim; Franz Esser; Horst Dollinger, both of Ingelheim am Rhein; Birgit Jung, Bingen am Rhein; Georg Speck, Ingelheim am Rhein; Erich Burger, Bingen am Rhein, all of Germany

[73] Assignee: Boehringer Ingelheim GmbH, Ingelheim am Rhein, Germany

[21] Appl. No.: 475,278

[22] Filed: Jun. 7, 1995

Related U.S. Application Data

[63] Continuation of Ser. No. 434,613, May 4, 1995.

[30] Foreign Application Priority Data

May 7, 1994 [DE] Germany ............... 44 16 255.3
Dec. 22, 1994 [DE] Germany ............... 44 45 939.4

[51] Int. Cl.$^6$ .................. A61K 31/405; A61K 31/40; C07D 403/12; C07D 207/12
[52] U.S. Cl. .................. 514/414; 514/305; 514/343; 514/397; 514/422; 514/423; 546/137; 546/279.1; 548/314.7; 548/467; 548/517; 548/518; 548/525; 548/527; 548/537
[58] Field of Search ................ 548/537, 467, 548/314.7, 517, 518, 525, 527; 514/414, 423, 397, 422, 305, 343; 546/137, 279.1

[56] References Cited

U.S. PATENT DOCUMENTS 5,596,000  1/1997  Esser et al. .............. 514/312

FOREIGN PATENT DOCUMENTS 443132   8/1991  European Pat. Off. .
482539   4/1992  European Pat. Off. .
9405693  3/1994  WIPO .

OTHER PUBLICATIONS

Maggi et al, *J. Auton. Pharmacol.* 13, pp. 23–93 (1993).
Rouissi et al, *Biochemical and Biophysical Research Communications*, 176 pp. 894–901 (1991).

Primary Examiner—Emily Bernhardt
Attorney, Agent, or Firm—Robert P. Raymond; Alan R. Stempel; Mary Ellen Devlin

[57] ABSTRACT

The invention relates to new amino acid derivatives of general formula I $$R^1\text{—}R^{11}\text{—}A^1B \qquad (I)$$

and the pharmaceutically acceptable salts thereof, wherein group B is —$A^2$—$NR^2R^3$ or $R^5$, and wherein $R^1$, $A^1$, $A^2$, $R^2$, $R^3$, $R^5$ and $R^{11}$ have the meanings described in the specification, as well as the preparation and use thereof. The novel compounds are valuable neurokinin (tachykinin) antagonists.

13 Claims, No Drawings

AMINO ACID DERIVATIVES, PROCESSES FOR THE MANUFACTURE THEREOF AND PHARMACEUTICAL COMPOSITIONS (II) CONTAINING THESE COMPOUNDS

This application is a continuation of prior pending application Ser. No. 08/434,613, filed May 4, 1995.

The invention relates to new amino acid derivatives of general formula I,

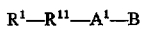
(I)

wherein B represents the group —$A^2$—$NR^2R^3$ or $R^5$, and the pharmaceutically acceptable salts thereof, processes for their preparation and pharmaceutical compositions containing these compounds. The compounds are valuable neurokinin (tachykinin)-antagonists.

European Patent Applications EP 394 989 and EP 443 132 as well as WO 94/05 693 disclose peptides with a neurokinin-antagonistic activity. The compounds according to the invention differ significantly from these peptides in the members $R^1$, $A^{2,}$ $R^5$ and

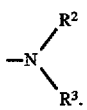

The abbreviations used for the amino acids in this specification and the Claims correspond to the conventional three letter code described for example in Europ. J. Biochem., 138, 9 (1984). The other abbreviations are defined as follows:

Boc=t-Butoxycarbonyl
Bzl=Benzyl
CDI=Carbonyldiimidazole
Cha=3-Cyclohexylalanine
DCCI=Dicyclohexylcarbodiimide
DCH=Dicyclohexylurea
HOBt=1-Hydroxybenzotriazole
Hpa=Homophenylalanine
Hyp=(2S,4R)-Hydroxyproline
Pal=3-(1-Pyrrolyl)alanine
THF=Tetrahydrofuran
TFA=Trifluoroacetic acid
Z=Benzyloxycarbonyl
Me=Methyl
Ac=Acetyl
Et=Ethyl
DMF=Dimethylformamide
DPPA=Diphenylphosphorylazide
PPA=Polyphosphoric acid
RT=ambient temperature
Mtr=4-Methoxy-2,3,6-trimethylbenzolsulphonyl
Trp(for)=formyl-protected Tryptophan
Met(O)=Methionine, wherein S is oxidized to form sulphoxide
Bum=N(II)-tert. butoxymethyl Unless explicitly indicated otherwise in the following text, the expression amino acid covers natural and unnatural amino acids, both the D- and L-forms, more particularly α-amino acids as well as the isomers thereof.

If an amino acid is given without prefix (e.g. Orn) this indicates the L-form of the amino acids. The D-form is explicitly indicated.

A simplified form is used for the illustration of the formulae. In this illustration of the compounds, all $CH_3$-substituents are represented by a single bond, for example

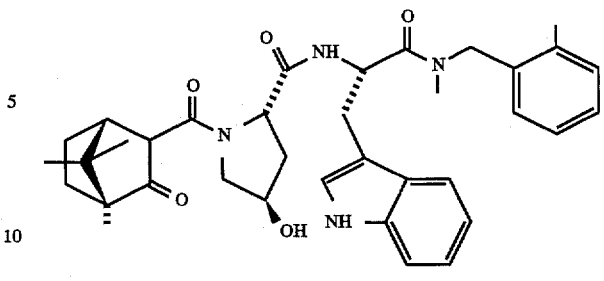

represents

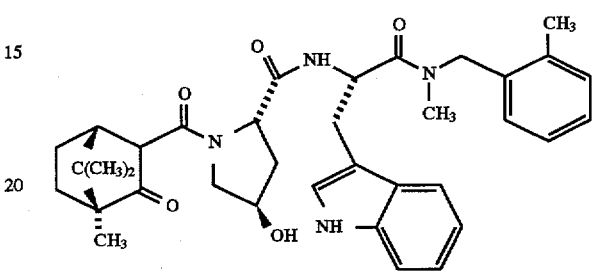

In the illustration of groups (e.g. $R^1$ or $A^2$), the $CH_3$—groups in the group are written in full. It is only in the groups derived from camphorcarboxylic acid and the derivatives thereof that the $CH_3$-groups bonded to the bridging carbon atom are represented by single bonds, for example group ($R^1$)

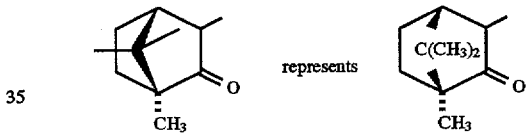

represents

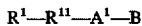

The invention relates to new amino acid derivatives of general formula I $R^1$—$R^{11}$—$A^1$—B   (I)

and the pharmaceutically acceptable salts thereof, wherein $R^1$ is a saturated or partially saturated 6-membered ring which consists of 6 carbon atoms or 5 carbon atoms and an O- or N-atom and which has, in the 2- or 3-position relative to $R^{11}$, an oxygen functionality which is =O, —OH or —O-($C_1$-$C_4$-alkyl), whilst the ring may also have a —$CH_2$—, —C($CH_3$)$_2$—, —C($C_2H_5$)$_2$— or —$CH_2$_$CH_2$— bridge, or, additionally to said bridge, may have a bond between two non-adjacent carbon atoms, and the un-bridged or bridged ring may also be substituted by 1 to 5 ($C_1$-$C_3$)-alkyl groups;

$R^{11}$ denotes —C(O)—, —$CH_2$—C(O)—, —$SO_2$— or —$CH_2$—$SO_2$—;

$A^1$ is D- or L-alanine (Ala), D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ(3,4)-Pro), D- or L-hydroxyproline (Pro (OH)) such as 3-hydroxyproline (Pro(3OH)) and 4-hydroxyproline (Pro(4OH)), D- or L-azetidine-2-carboxylic acid (Azt), D- or L-thioproline (Tpr), D- or L-aminoproline (Pro(NH$_2$)) such as 3-aminoproline (Pro (3NH$_2$)) and 4-aminoproline (Pro (4NH$_2$)), D- or L-pyroglutamic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Asn), D- or L-lysine (Lys), D- or L-arginine (Arg), D- or L-histidine (His), D- or L-ornithine (Orn), D- or L-hydroxy piperidine carboxylic acid such as 5-hydroxypiperidine-2-carboxylic acid, D- or L-mercaptoproline (Pro(SH)) such as 3-mercaptoproline (Pro(3SH)) and 4-mercaptoproline (Pro(4SH)), Tpr(O), Met (O), Tpr($O_2$) or Met($O_2$), and the geometric isomers thereof, whereby the hydroxy and amino groups contained therein may be protected by standard protecting groups (e.g. acyl, carbamoyl or aralkyl (in particular benzyl));

B is group —$A^2$—$NR^2R^3$ or —$R^5$;

$A^2$ is a lipophilic α-amino acid which contains a phenyl, mono-, di- or tri-substituted phenyl, heteroaryl, cyclohexyl or cyclopentyl group, a naphthyl group or a mono- or di-$C_{1-3}$-alkylamino group, and this cyclic group or amino group is separated by a 1- to 8-membered chain from the backbone of the amino acid, whereby the substituents of the phenyl group may, independently of each other, be halogen, trihalomethyl, alkoxy, alkyl, cyano or 1-pyrrolidinyl and whereby in the 1- to 8-membered chain, the members of the chain may be —$CHR^4$—, —C(O)—, —O—, —S— and/or —$NR^4$— which are arranged such that they result in one of the following three types of chains

—$(CHR^4)_{1-8}$—

—$(CHR^4)_{0-p}$—$G^1$—$(CHR^4)_{0-q}$—

(—$CHR^4)_{1-p}$—$G^2$—$(CHR^4)_{0-q}$— wherein $G^1$ is —C(O)O— or —C(O)—$NR^4$—, $G^2$ is —O—, —S—, —$NR^4$—C(O)—O—, —$NR^4$—C(O)—, —$NR^4$—C(O)—$NR^4$— or —O—C(O)—$NR^4$— and p and q are whole numbers from 1 to 6 which are chosen such that the total number of the chain members is 1 to 8, and $R^4$ is hydrogen, alkyl, aryl or aralkyl, wherein aryl is phenyl, mono-, di- or tri-substituted phenyl or naphthyl; the substituents of the phenyl group are, independently of each other, halogen, trihalomethyl, alkoxy, alkyl or cyano, and the alkyl group contains 1 to 3 carbon atoms; (whereby, if one chain contains more than one —$CHR^4$-group, $R^4$ can only be alkyl, aryl or aralkyl in one of these —$CHR^4$-groups)

or $A^2$ is Leu, Ile, Nle, Val, Met or one of the groups

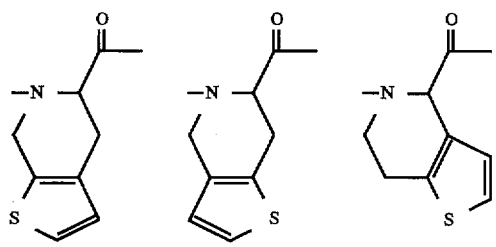

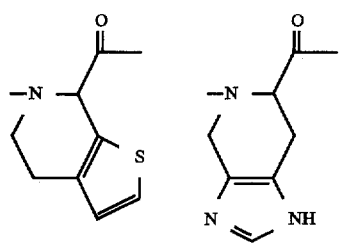

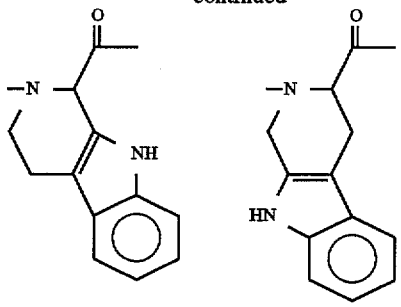

and

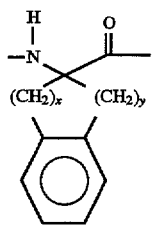

(wherein x and y independently of each other are 1 or 2);

$R^2$ and $R^3$ independently of each other are alkyl, arylalkyl, heteroaryl or hydroxy (wherein aryl is phenyl, mono-, di- or trisubstituted phenyl or naphthyl; the substituents of the phenyl group are, independently of each other, halogen, trihalomethyl, alkoxy, alkyl, alkylthio, hydroxy, nitro, trifluoromethoxy, dialkylamino or cyano or 2 adjacent positions of the phenyl group are linked by —O—$(CH_2)_{1}$ or $_2$—O—; heteroaryl is indolyl, pyridyl, pyrrolyl, imidazolyl or thienyl; and the alkyl or alkoxy group contains 1 to 3 carbon atoms) or the group

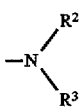

is a ring of general formula

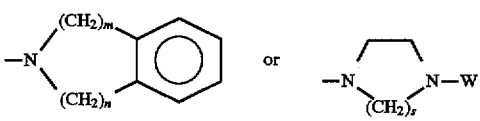

wherein m and n are each 0, 1, 2 or 3, whereby the sum thereof is 2, 3, 4 or 5, s is 2 or 3, W is the group

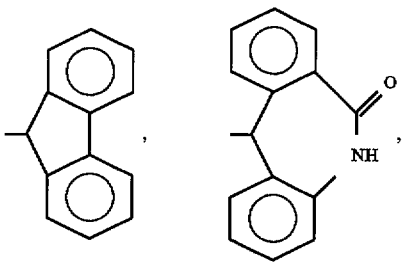

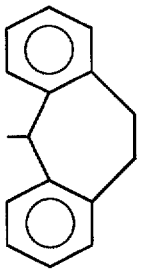

$(CH_2)_{0-2}$-aryl, $CH(aryl)_2$, cyclopentyl, $(CH_2)_{0-2}$-cyclohexyl, pyridyl or

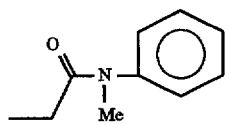

(wherein aryl is phenyl, mono-, di- or trisubstituted phenyl or naphthyl; the substituents of the phenyl group independently of each other are halogen, trihalomethyl, alkoxy, alkyl, cyano, hydroxy, nitro, —$CO_2CH_3$, —$CO_2C_2H_5$, or alkylthio, or 2 adjacent positions of the phenyl group are linked by —O—$(CH_2)_{1-2}$—O— and alkyl contains 1 to 3 carbon atoms);

$R^5$ is an amine of formula

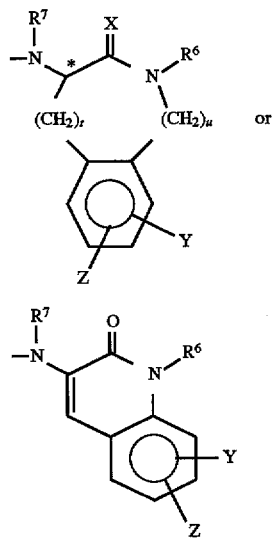

wherein $R^6$ is aralkyl, diarylalkyl (in these groups aryl is phenyl or naphthyl and alkyl is $(C_{1-5})$alkyl), heteroaryl-$(C_{1-5})$alkyl (wherein heteroaryl is 2-, 3- or 4-pyridyl or 2- or 3-thienyl), phenylamino-$(C_{1-5})$alkyl, naphthylamino-$(C_{1-5})$alkyl or N-phenylalkylpiperidinyl (wherein the phenyl groups listed are unsubstituted or have 1, 2 or 3 substituents which are, independently of each other, $(C_{1-5})$alkyl, preferably methyl, $(C_{1-5})$alkoxy, preferably methoxy, dimethylamine, halogen, trifluoromethyl, —CN or —$OCF_3$);

$R_7$ is hydrogen or $(C_{1-5})$-alkyl;

X is O or $H_2$;

Y and Z independently of each other are hydrogen, $(C_{1-5})$alkyl; $(C_{1-5})$alkyloxy, benzyloxy (wherein the phenyl group is unsubstituted or has 1, 2 or 3 substituents which are independently of each other $(C_{1-5})$alkyl, preferably methyl, $(C_{1-5})$alkoxy, preferably methoxy, dimethylamine, halogen, trifluoromethyl, —CN or —$OCF_3$), —$OCF_3$, halogen, —$CF_3$, —CN, —$CH_2NH_2$, —$CONH_2$, N-$(C_{1-4}$-alkyl$)_2$, NH-$(C_{1-4})$alkylcarbonyl, N-$(C_{1-5})$alkyl-N-$(C_{1-4})$alkylcarbonyl, $NH_2$ or NH-$(C_{1-5})$alkyl or if Y and Z are in a vicinal position to one another, both together represent —$OCH_2O$—, —$OCH_2CH_2O$— or $(CH)_4$;

t and u have one of the following meanings
(a) t and u are zero
(b) t is one and u is zero
(c) t and u are both one
(d) t is two and u is zero;

and if t is one and u is zero, $R^5$ is also an amine of formula IV

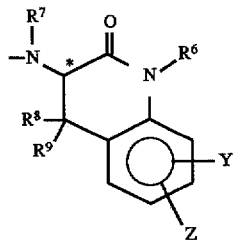

wherein $R^6$, $R^7$, Y and Z have the above meanings and $R^8$ is hydrogen and $R^9$ is hydroxy, $(C_{1-5})$alkoxy, phenyl-$(C_{1-5})$alkyloxy, naphthyl-$(C_{1-5})$ alkyloxy or $(C_{1-4})$alkylcarbonyl, or wherein $R^8$ and $R^9$ together are oxygen or —$OCH_2CH_2O$—;

and the chirality of C* may be R or S.

The compounds according to the invention are valuable neurokinin (tachykinin)-antagonists which have substance P-antagonism, but also neurokinin A and neurokinin-B antagonistic properties. They are useful for treating and preventing neurokinin-mediated diseases.

Compounds of general formula I may have acid groups, mainly carboxyl groups or phenolic hydroxy groups, and/or basic groups such as guanidino or amino functionalities. Therefore, compounds of general formula I may be present either as internal salts, as salts with pharmaceutically acceptable inorganic acids such as hydrochloric acid, sulphuric acid, phosphoric acid, sulphonic acid or organic acids (e.g. maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as diethylamine, triethylamine, triethanolamine and the like.

The chiral centres in the new amino acid derivatives may have an R—, S- or R,S-configuration.

The expression "partially saturated 6-membered ring" used in the definition of $R^1$ represents a 6-membered ring which contains two double bonds or preferably one double bond.

The bridged or unbridged ring described in the definition of $R^1$ may contain 1 to 5 $(C_1$–$C_3)$-alkyl groups (preferably methyl groups). Here, it must be noted that each of these alkyl groups substitutes for one or two H-atoms of the $CH_2$-groups forming the ring, and that in two adjacent $CH_2$-groups a maximum of 3 H-atoms is substituted by alkyl groups. This means that the group $R^1$ contained in e.g. compound 1 has a maximum of 5 alkyl groups in the ring (in addition to the two methyl groups of the bridge) and that the group $R^1$ in compound 22, has a maximum of 4 alkyl groups.

The above bridge preferably connects positions 1 and 4, 2 and 5 or especially 3 and 6, based on position 1 of the ring being bonded to $R^{11}$.

Preferably, the bridge connects 2 carbon atoms of the ring. If $R^1$ is a heterocyclic ring containing N, $R^1$ is preferably bonded to $R^{11}$ via a carbon atom.

The expression "heteroaryl group" contained in the definition of $A^2$ represents a mono-, bi- or tricyclic aromatic ring system which contains 1 or 2 heteroatoms, namely one or two nitrogen atoms or one nitrogen atom and one sulphur atom. The group may optionally contain 1 or 2 substituents ($C_{1-3}$alkyl) or one oxo group or one alkoxy group.

Examples of suitable heteroaryl groups are

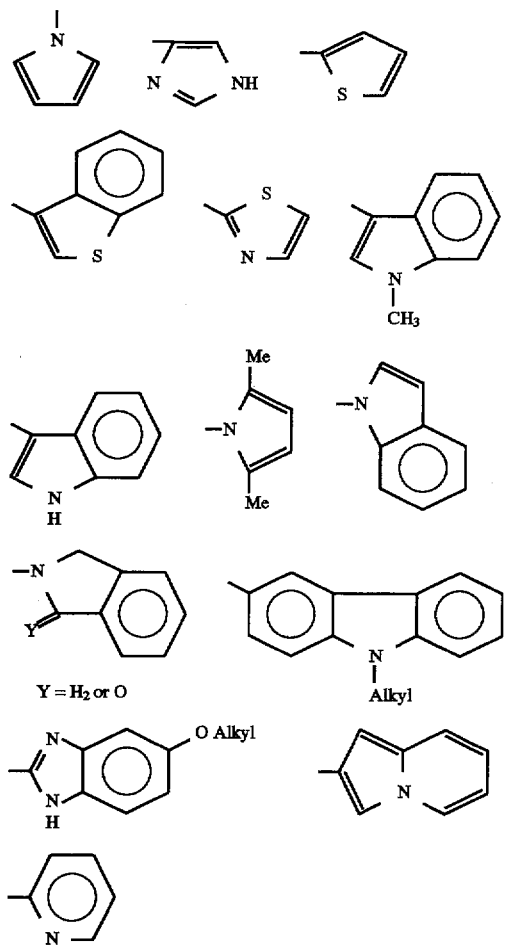

It must be noted that the above heteroaryl groups may also be bound to the chain in positions other than those mentioned.

As mentioned above, the "1- to 8-membered chain" contained in $A^2$ comprises 1 to 8 members denoting the following groups: —CHR$^4$—, —C(O)—, —O—, —S—, —NR$^4$—. The chain is bound to the α-carbon atom of the amino acid ($A^2$).

$R^4$ represents (as indicated above) hydrogen, alkyl, aryl or aralkyl. $R^4$ is preferably hydrogen, methyl or phenyl.

Examples of suitable chains are

—(CH$_2$)$_{1-4}$—
—CH$_2$—O—CH$_2$—, —CH$_2$—O—
—CH$_2$—S—CH$_2$—, —CH$_2$—S—
—CH(CH$_3$)—O—CH$_2$—, —CH(CH$_3$)—O—
—(CH$_2$)$_{1-2}$—C(O)—O—CH$_2$—, —C(O)—NH—
—(CH$_2$)$_4$—NH—C(O)—O—CH$_2$—
—CH$_2$—C(O)—NH—
—CH$_2$—C(O)—NH—CH$_2$—
—CH$_2$—C(O)—N(CH$_3$)—CH$_2$—
—CH$_2$—C(O)—O—
—CH$_2$—NH—C(O)—CH$_2$—
—CH$_2$—NH—C(O)—O—
—CH$_2$—NH—C(O)—O—CH$_2$—
—CH$_2$—NH—C(O)—NH—
—(CH$_2$)$_2$—C(O)—NH—(CH$_2$)$_2$—
—(CH$_2$)$_4$—NH—C(O)—CH$_2$—
—(CH$_2$)$_3$—NH—C(O)—O—CH$_2$—

The chain contains preferably 1 to 5, more preferably 1 to 4 members.

Those compounds of formula I, according to the invention, are preferred, wherein $R^1$ and $R^{11}$ have the above meanings, $A^1$ is D- or L-alanine (Ala), D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ(3,4)-Pro), D- or L-hydroxyproline (Pro(OH)) such as 3-hydroxyproline (Pro(3OH)) and 4-hydroxyproline (Pro(4OH)), D- or L-azetidine-2-carboxylic acid (Azt), D- or L-thioproline (Tpr), D- or L-aminoproline (Pro(NH$_2$)) such as 3-aminoproline (Pro(3NH$_2$)) and 4-aminoproline (Pro(4NH$_2$)), D- or L-pyroglutamic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Asn), D- or L-lysine (Lys), D- or L-arginine (Arg), D- or L-histidine (His), D- or L-ornithine (Orn), D- or L-hydroxy piperidine carboxylic acid such as 5-hydroxypiperidine-2-carboxylic acid, D- or L-mercaptoproline (Pro(SH)) such as 3-mercaptoproline (Pro(3SH)) and 4-mercaptoproline (Pro(4SH)), Tpr(O), Met(O), Tpr(O$_2$) or Met(O$_2$), and the geometric isomers thereof, whereby the hydroxy and amino groups contained therein may be protected by standard protecting groups (e.g. acyl, carbamoyl or aralkyl (in particular benzyl));

and if B is group —A$^2$—NR$^2$R$^3$ $A^2$ is a lipophilic amino acid which contains a phenyl-, mono-, di- or trisubstituted phenyl-, heteroaryl-, cyclohexyl- or cyclopentyl group or a mono- or di-$C_{1-3}$-alkylamino group, and this cyclic group or amino group is separated by a 1- to 8-membered chain from the backbone of the amino acid (whereby the substituents of the phenyl group independently of each other are halogen, trihalomethyl, alkoxy, alkyl, cyano or 1-pyrrolidinyl and the chain is defined as in claim 1) or $A^2$ is Leu, Ile, Nle, Val, Met or one of the groups

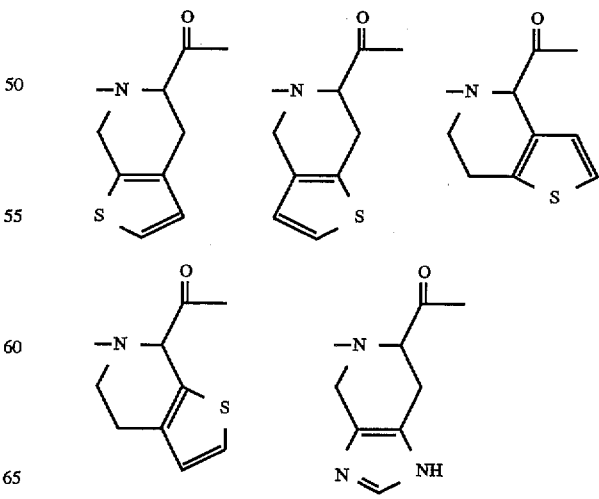

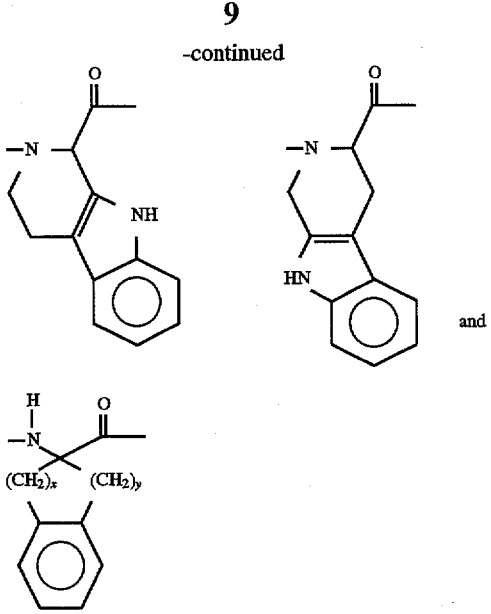

(wherein x and y independently of each other are 1 or 2);

R² and R³ independently of each other are alkyl, arylalkyl, heteroaryl or hydroxy (wherein aryl represents phenyl, mono-, di- or trisubstituted phenyl or naphthyl; the substituents of the phenyl group independently of each other denote halogen, trihalomethyl, alkoxy, alkyl or cyano; heteroaryl represents indolyl, pyridyl, pyrrolyl, imidazolyl or thienyl; and the alkyl or alkoxy groups contains 1 to 3 carbon atoms) or the group

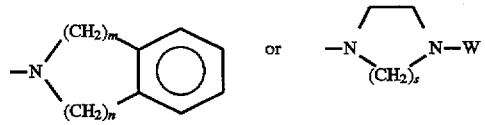

is a ring of general formula

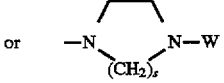

wherein m, n and s are defined as in claim 1 and
W is the group

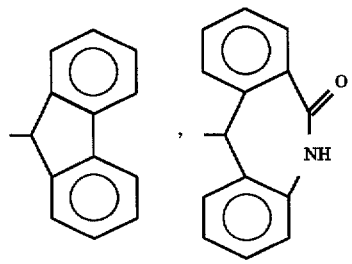

—(CH₂)₀₋₂-aryl, CH(aryl)₂, cyclopentyl or (CH₂)₀₋₂-cyclohexyl (wherein aryl represents phenyl, mono-, di- or trisubstituted phenyl or naphthyl; the substituents of the phenyl group independently of each other are halogen, trihalomethyl, alkoxy, alkyl or cyano).

Of the compounds, according to the invention, of formula Ia $$R^1—R^{11}—A^1—A^2—NR^2R^3 \quad \text{Ia}$$

those are preferred wherein

R¹ and R¹¹ have the above meanings and/or

A¹ is an amino acid which carries one or 2 polar functional group(s) in the side chain such as OH, COOH, NH₂, guanidine, CONH₂, SH; particularly wherein the functional group in the side chain of A¹ is OH and/or wherein A¹ is Pro, 4-hydroxyproline, 3-hydroxyproline, Ser, Thr, Trp(For) or Tyr; preferably 4-hydroxyproline with 2-S-configuration, particularly

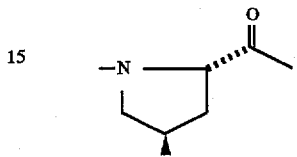

and/or wherein A² represents an acyclic or cyclic amino acid such as (O-benzyl)Ser, (O-subst. benzyl)Ser, (O-benzyl)Thr, cyclohexylalanine, homophenylalanine, 3-(1-pyrrolyl)-alanine, 3-(2,5-dimethyl-1-pyrrolyl)alanine, 3-(1-indolyl) alanine, 2-amino-4-(1-pyrrolyl)-butyric acid, 2-amino-5-(1-pyrrolyl)valeric acid, 2-amino-6-(1-pyrrolyl)caproic acid, Leu, Lys(Z), 3-(2-thienyl)alanine, 3-(3-benzothienyl) alanine, 3(1-isoindolinonyl)alanine, (O-benzyl)Asp, (O-benzyl)Glu, Trp, (N-Me)Trp, His, 3-(2-thiazolyl)-alanine, or 3-dimethylamino-alanine, -(O-methyl)Tyr, 2-naphthylalanine,

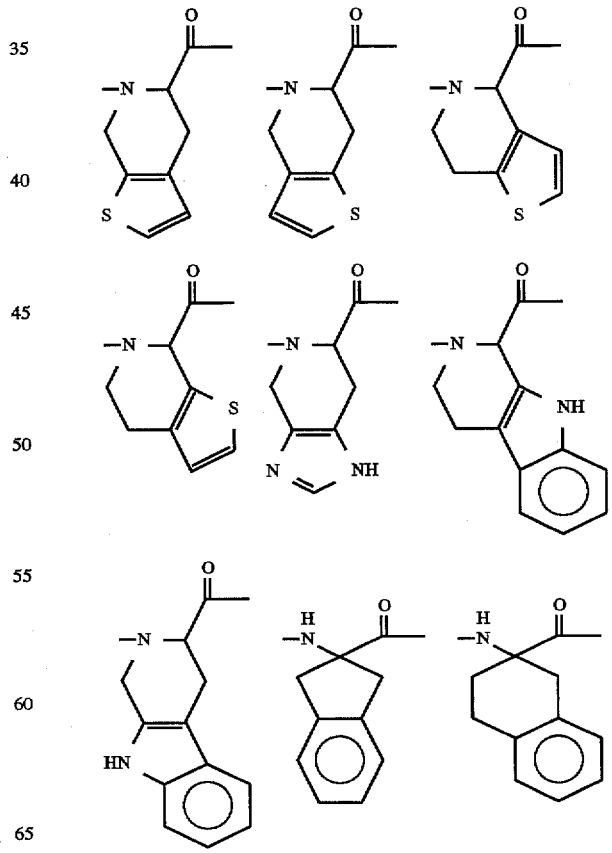

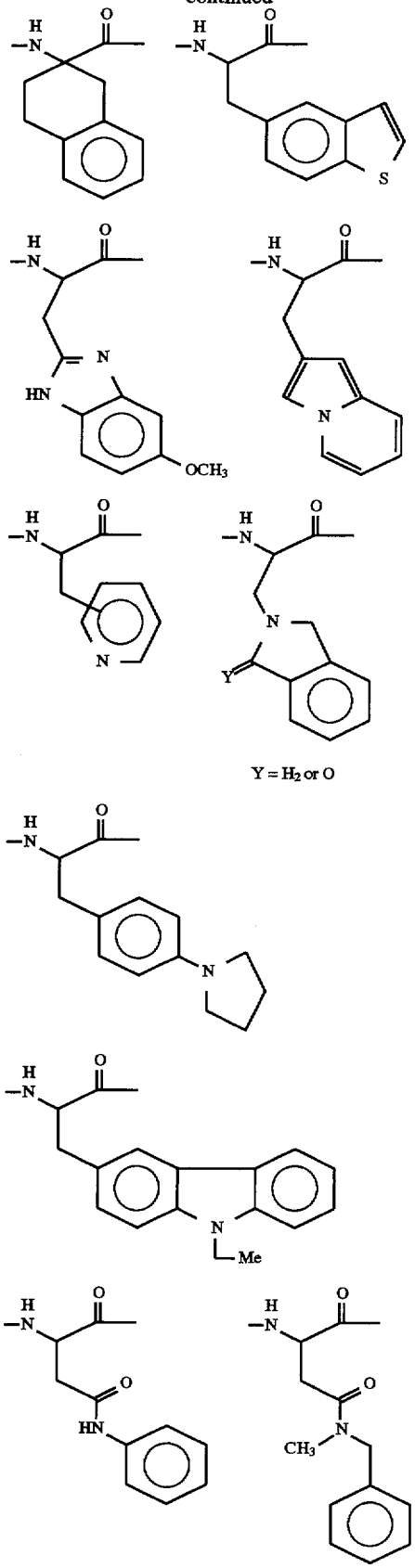
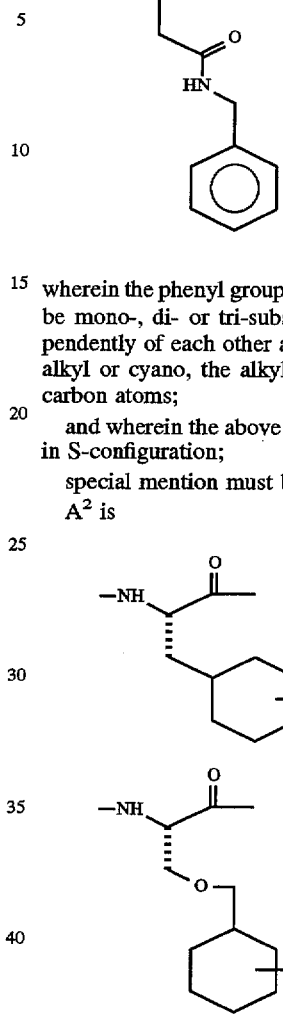

-continued

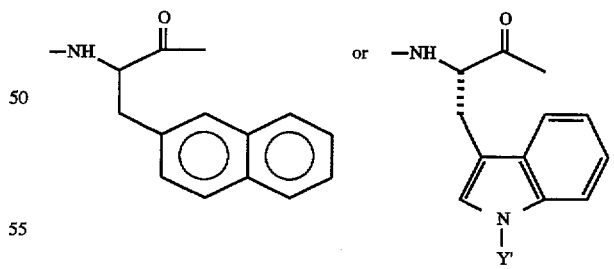

wherein the phenyl groups contained in the amino acids may be mono-, di- or tri-substituted and the substituents independently of each other are halogen, trihalomethyl, alkoxy, alkyl or cyano, the alkyl or alkoxy group contains 1 to 3 carbon atoms;

and wherein the above amino acids are preferably present in S-configuration;

special mention must be made of compounds wherein $A^2$ is or preferably and/or wherein $R^2$ and $R^3$ independently of each other represent methyl, benzyl, phenethyl (wherein the phenyl groups contained therein are substituted by one or two methyl or methoxy groups) or pyridylmethyl;

preferably a compound wherein $R^2$ is methyl and $R^3$ is benzyl or alkoxybenzyl, more particularly wherein $R^3$ is 2-methylbenzyl; or wherein the group

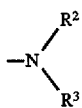

represents a ring

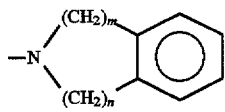

wherein m is 1 and n is 1 or 2;

or wherein the group

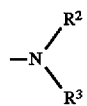

is a ring

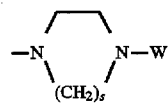

wherein s is 2 or 3 (preferably 2) and W is as hereinbefore defined;

preferably wherein W is cyclohexyl, phenyl, CH(phenyl)$_2$, naphtyl or pyridyl, wherein the phenyl groups are substituted;

wherein if W is phenyl, this is preferably monosubstituted by —CO$_2$CH$_3$, —CO$_2$C$_2$H$_5$, halogen, alkoxy, alkyl, cyano, hydroxy, nitro or alkylthio, particularly by methoxy, chlorine, methyl, ethyl, cyano, hydroxy, nitro or methylthio, preferably by methoxy, chlorine, methyl, cyano or methylthio, wherein the substituent of the phenyl group is preferably in position 2 and if W represents the group —CH(phenyl)$_2$, the phenyl groups are substituted by one halogen each, preferably by fluorine, wherein in the —CH(phenyl)$_2$ group the two phenyl groups are preferably substituted identically, preferably in p-position.

Of the compounds, according to the invention, of formula Ib

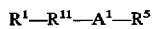

$R^1$—$R^{11}$—$A^1$—$R^5$  Ib those are preferred wherein $R^1$ and $R^{11}$ have the above meanings and/or $A^1$ is an amino acid which carries one or 2 polar functional group(s) in the side chain such as OH, COOH, NH$_2$, guanidine, CONH$_2$, SH; particularly wherein the functional group in the side chain of $A^1$ represents OH and/or wherein $A^1$ is Pro, 4-hydroxyproline, 3-hydroxyproline, Ser, Thr, Trp(For) or Tyr; preferably 4-hydroxyproline with 2-S-configuration, particularly

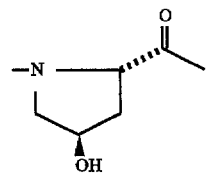

Of the compounds according to the invention, those are preferred wherein $R^5$ is a group of general formula II

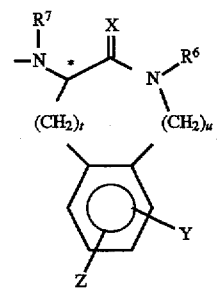

particularly those wherein t is one and u is zero or t is two and u is zero or t and u are both one and $R^6$, $R^7$, X, Y and Z are specified as hereinbefore.

Special mention must be made of those compounds wherein $R^6$ is benzyl or methoxybenzyl and/or wherein $R^7$ is hydrogen and/or wherein X is oxo and/or wherein Y and Z independently of each other represent methoxy, hydrogen, CF$_3$ or tert.butyl or together represent —(CH)$_4$—.

Of the above compounds those are preferred wherein $R^1$ is

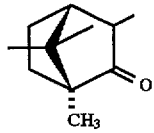

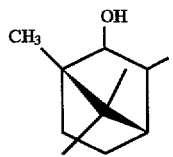

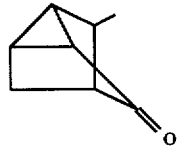

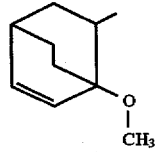

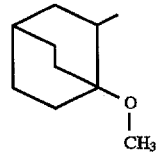

-continued

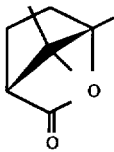

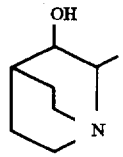

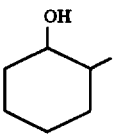

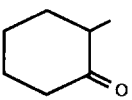

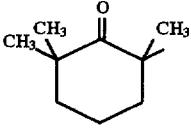 or

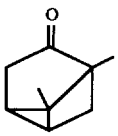

preferably

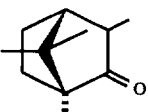

and $R^{11}$ is —$CH_2SO_2$— or preferably —C(O)—. The above amino acids are preferably in the S-configuration.

Test results of the compounds according to the invention:

The receptor affinity at the $NK_1$-receptor (substance P-receptor) was determined with cloned $NK_1$-receptors on human lymphoblastoma cells (IM-9), whereby the displacement of $^{125}$I-labelled substance P is measured. The $NK_2$-binding test is carried out on transfixed A20 cells which represent the human $NK_2$ receptor. The displacement of $^{125}$I-BN-neusolinine A is determined. The $IC_{50}$-values thus obtained are:

| Compound | $NK_1$ [nm] | $NK_2$ [nM] |
|---|---|---|
| 1 | 3.1 | 21 |
| 2 | 3.6 | 21 |
| 3 | 3.0 | 65 |
| 4 | 5.0 | 110 |
| 5 | 11 | 117 |
| 6 | 45 | |
| 7 | 0.45 | 44 |
| 8 | 3.0 | 18 |
| 9 | 17 | |
| 10 | 200 | |
| 11 | 3.2 | |
| 12 | 5.6 | |
| 13 | 105 | 780 |
| 14 | 3.1 | 240 |
| 15 | 3.2 | 38 |
| 16 | 0.7 | 19 |
| 17 | 7 | 93 |
| 18 | 8 | 16 |
| 19 | 26 | 600 |
| 20 | 26 | 350 |
| 21 | 20 | 130 |
| 22 | 25 | 1300 |
| 23 | 14 | 140 |
| 24 | 3.3 | 1240 |
| 25 | 18.0 | 880 |
| 26 | 28 | |
| 27 | 0.5 | 450 |
| 28 | 23 | 1500 |
| 42 | 1.2 | 54 |
| 43 | 1.2 | 21 |
| 44 | 5.1 | 39 |
| 45 | 4.9 | 59 |
| 47 | 3.2 | 57 |

List of Compounds:

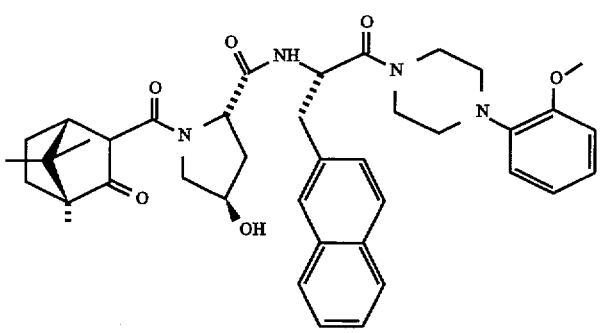

1

-continued
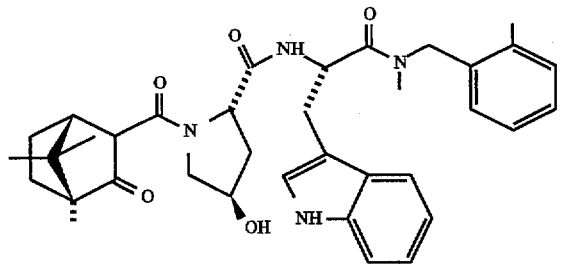
2
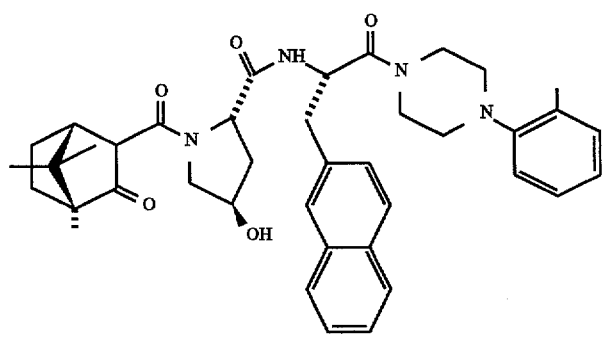
3
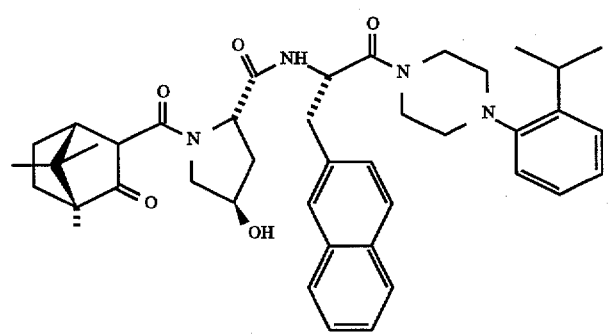
4
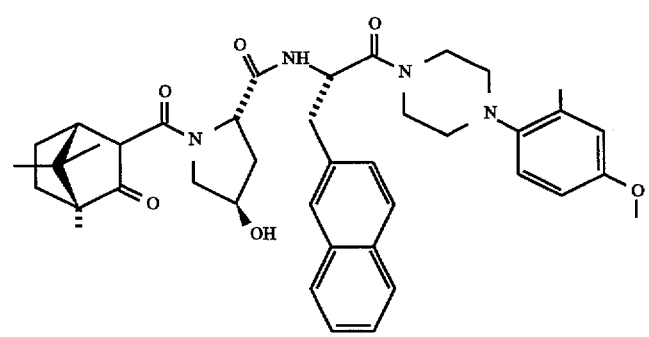
5
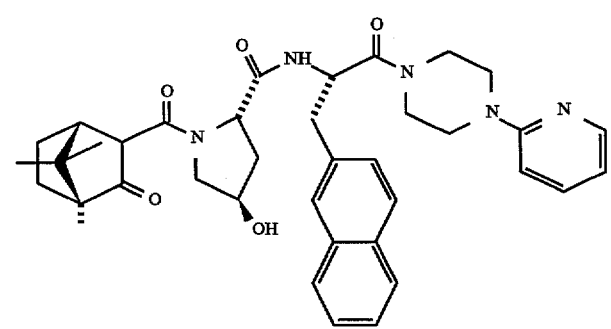
6

-continued
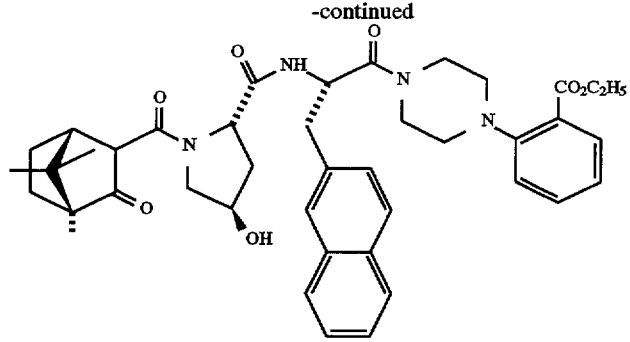
7
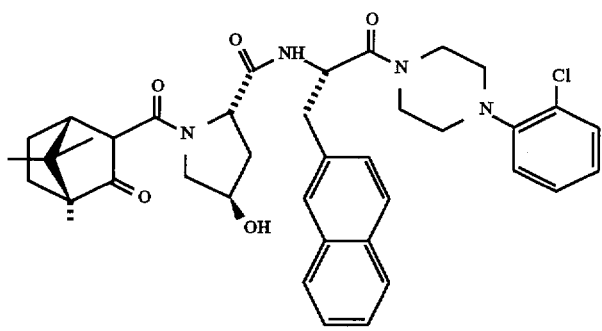
8
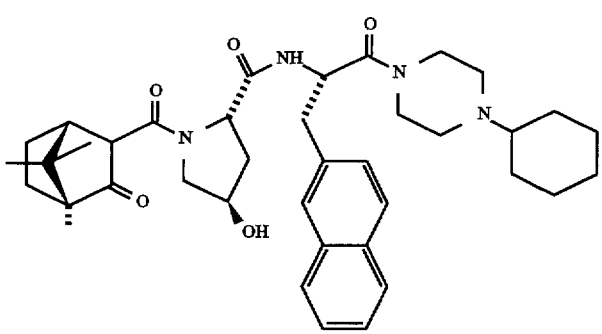
9
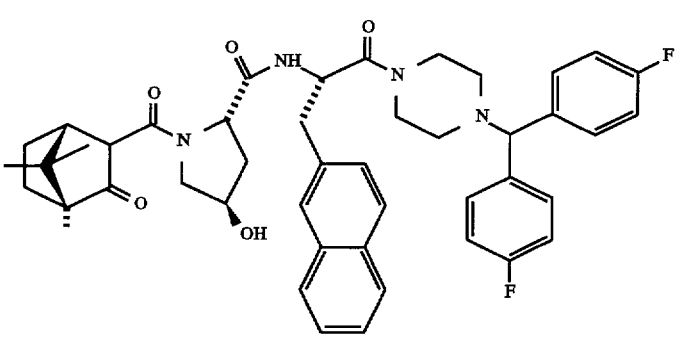
10
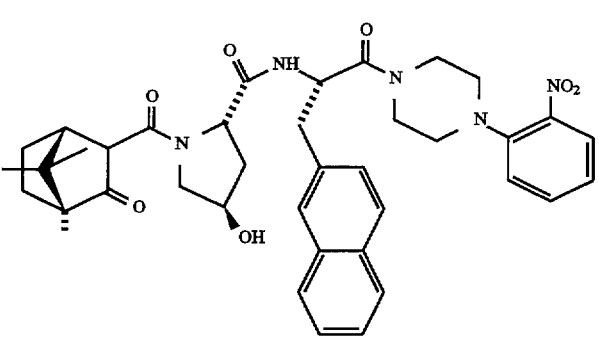
11

-continued
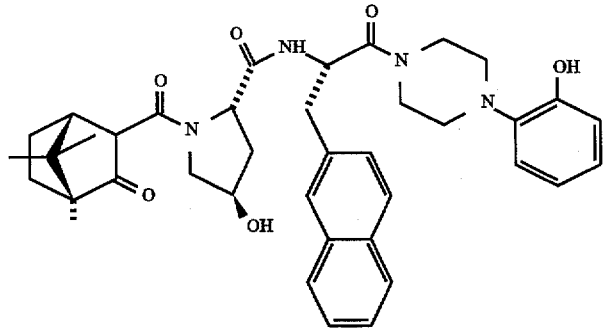
12
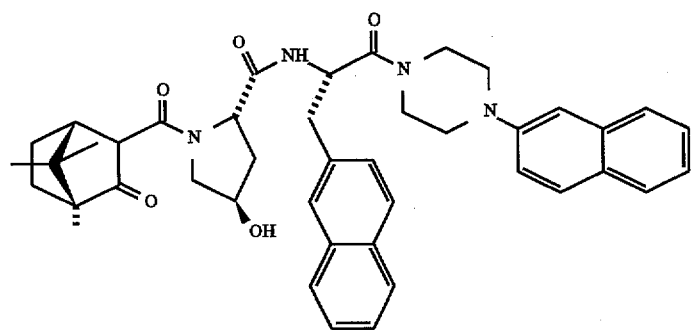
13
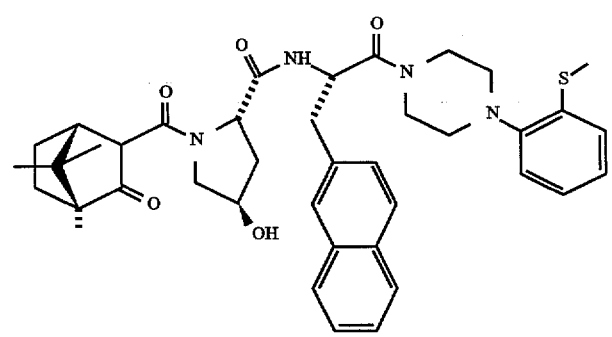
14
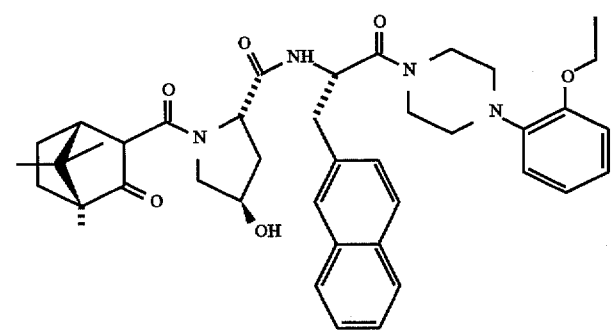
15
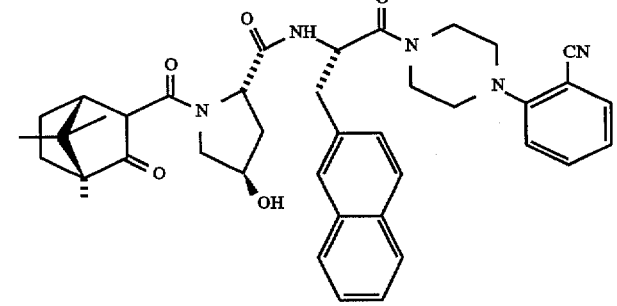
16

-continued
17
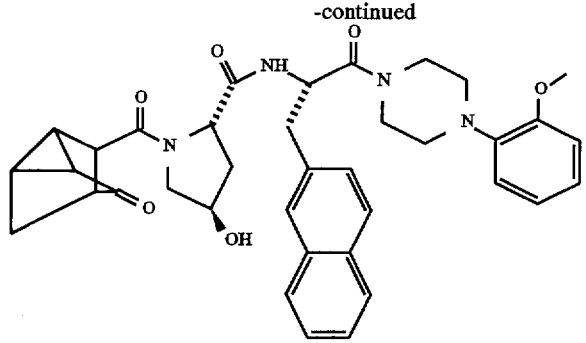
18
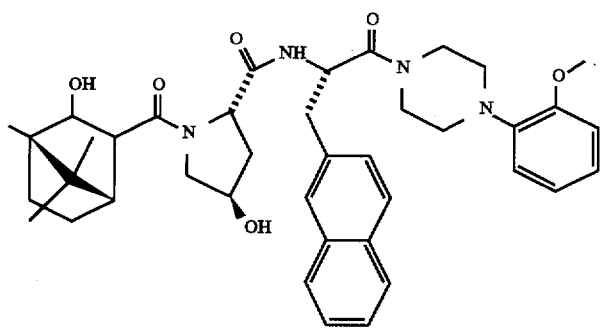
19
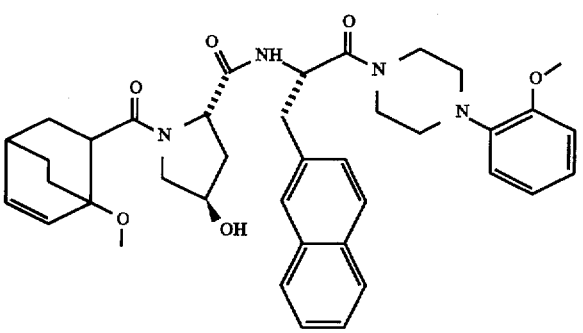
20
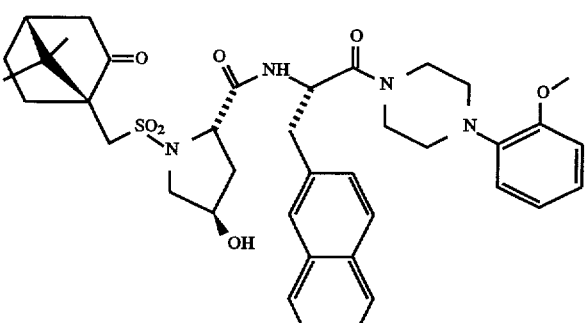
21
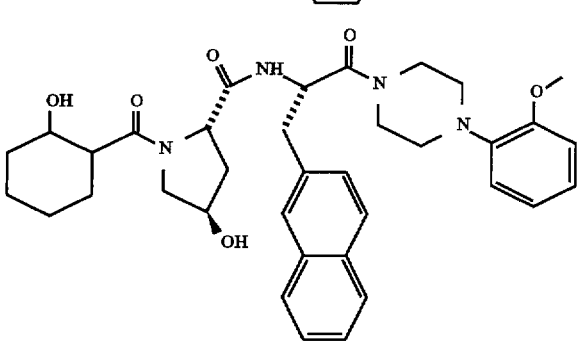

-continued
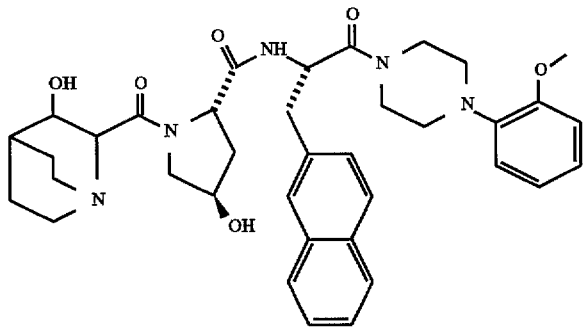
22
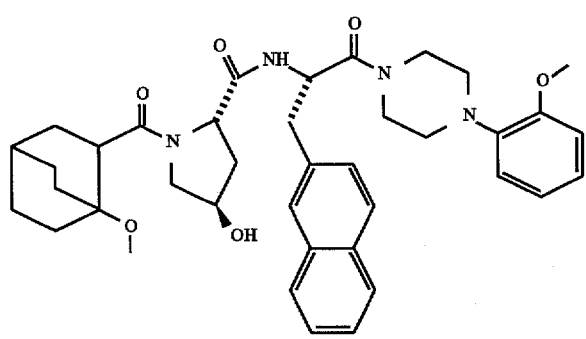
23
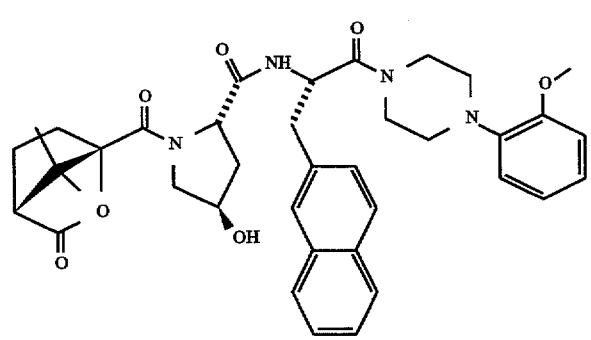
24
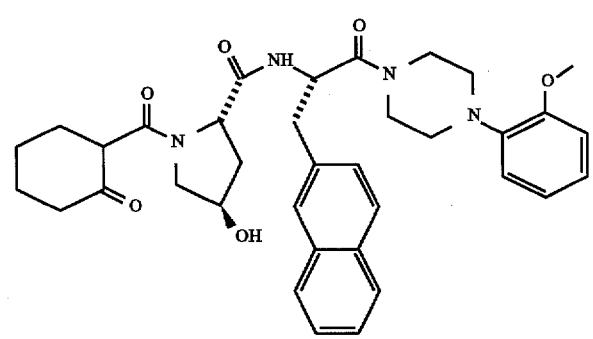
25
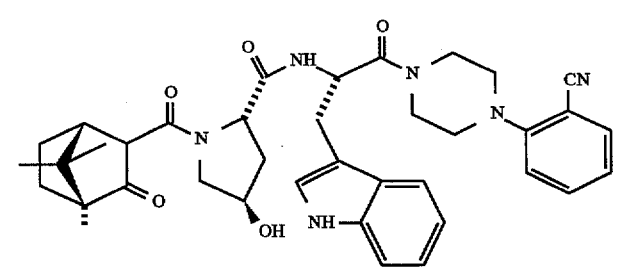
26

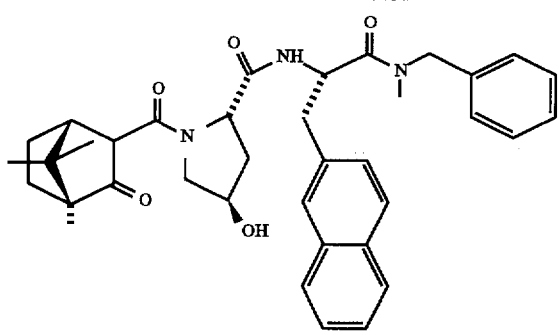
27
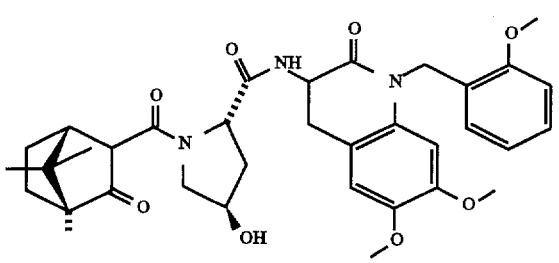
28
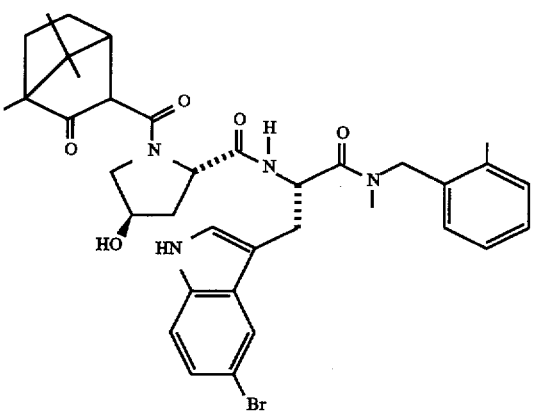
29
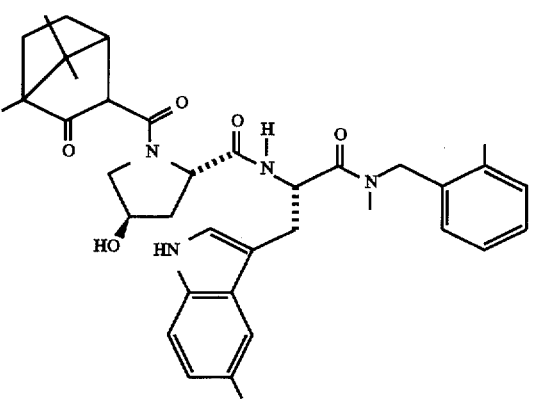
30

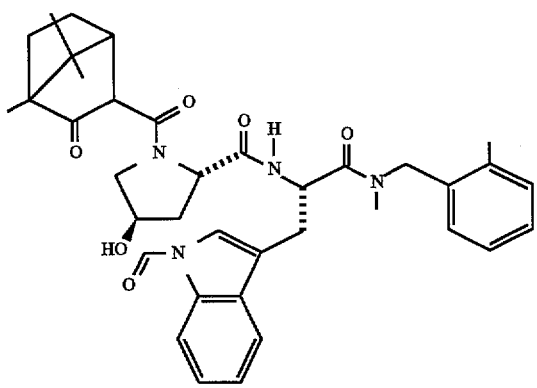
31
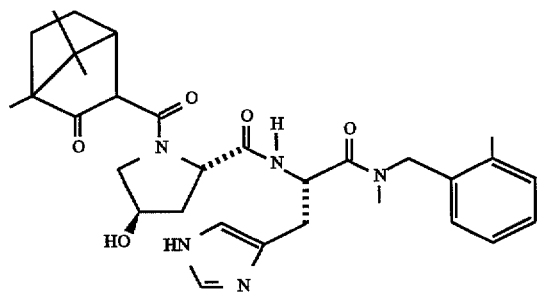
32
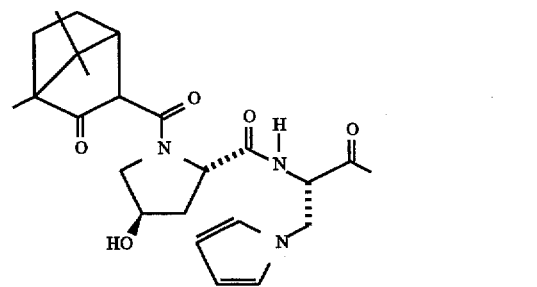
33
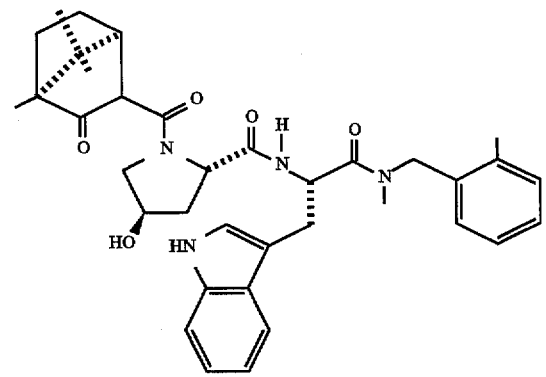
34

35
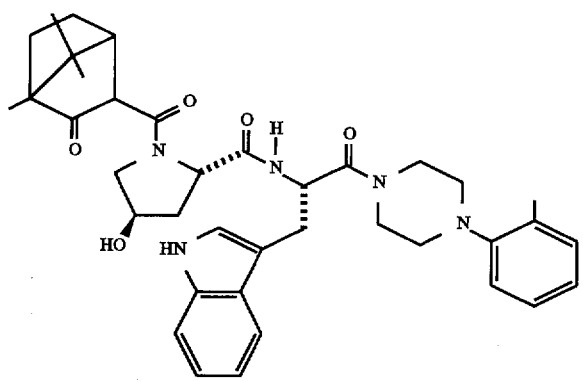
37
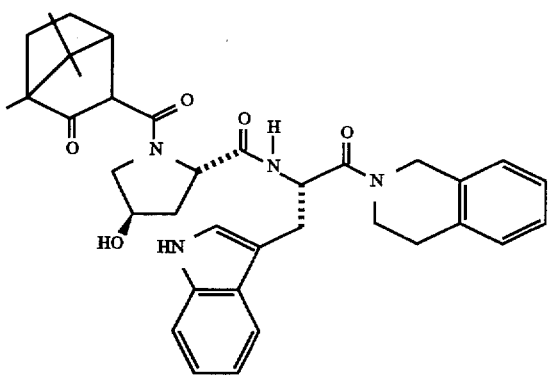
38
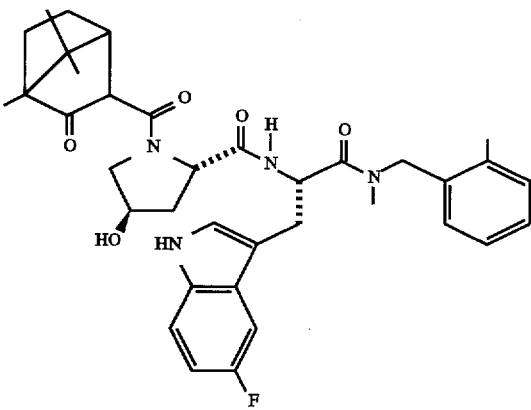
39
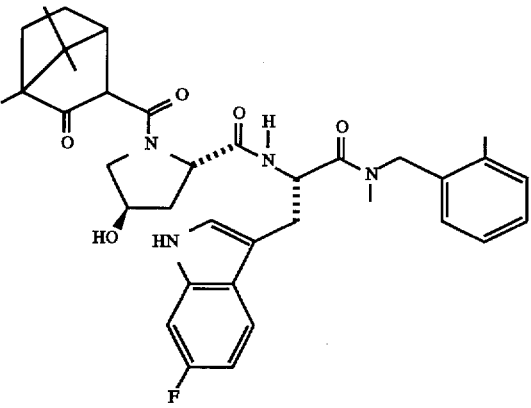

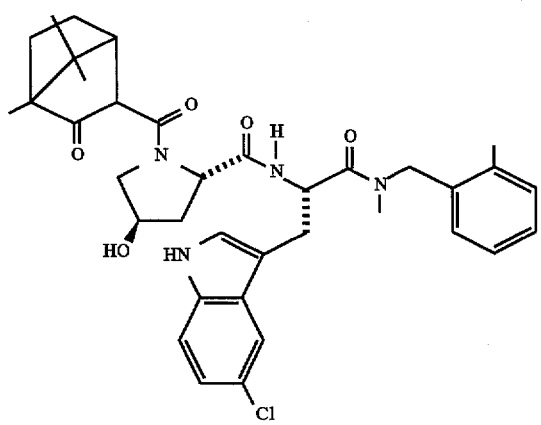
40
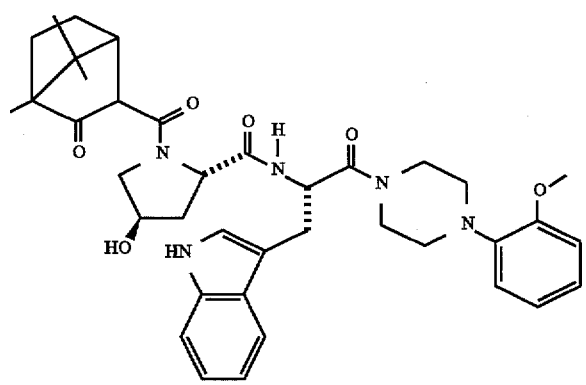
41
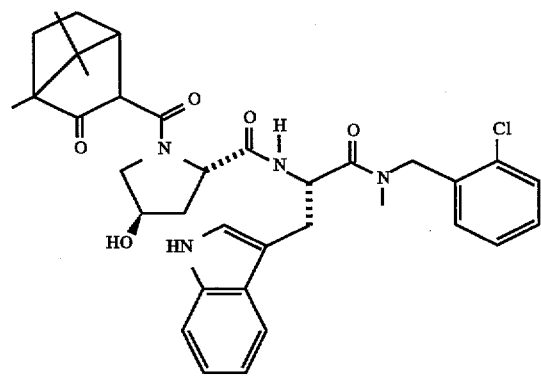
42
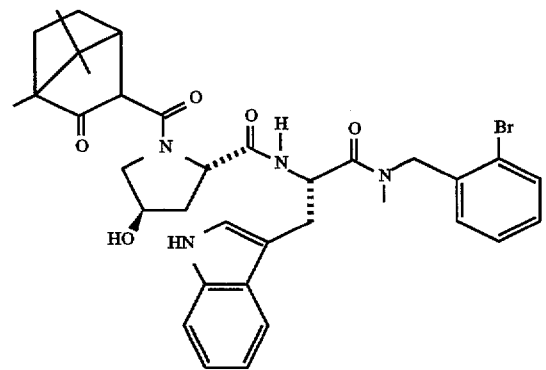
43

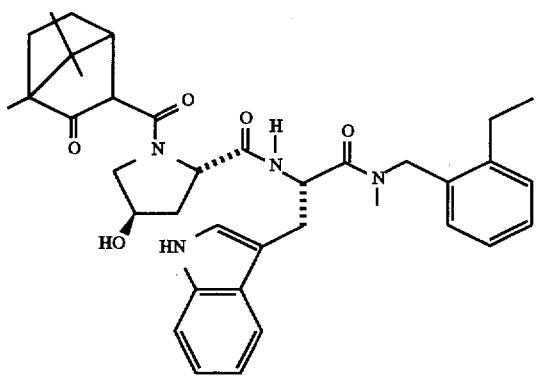
44
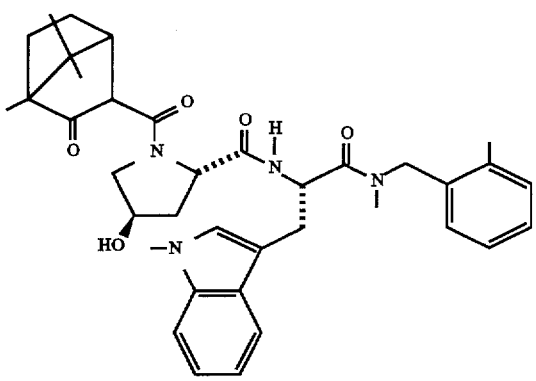
45
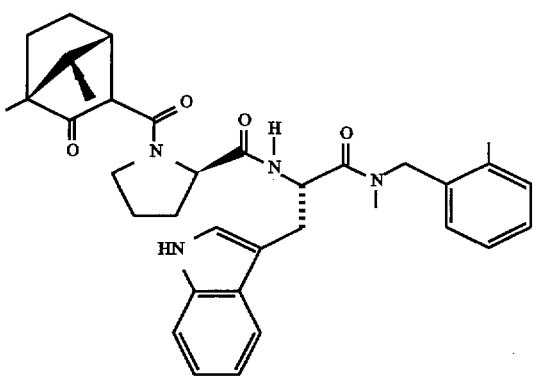
46
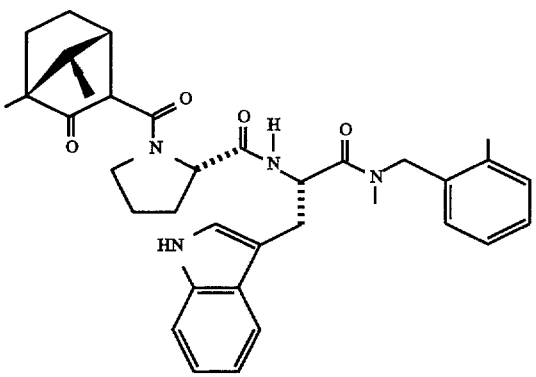
47

-continued
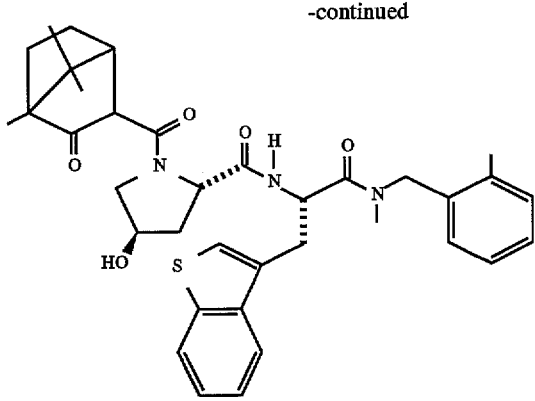
48
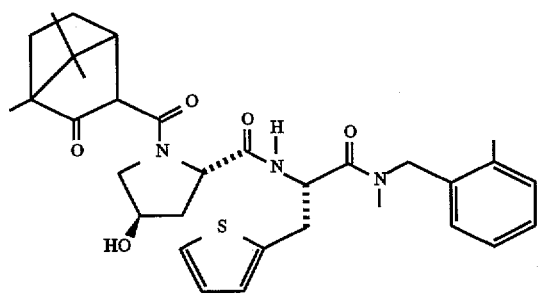
49
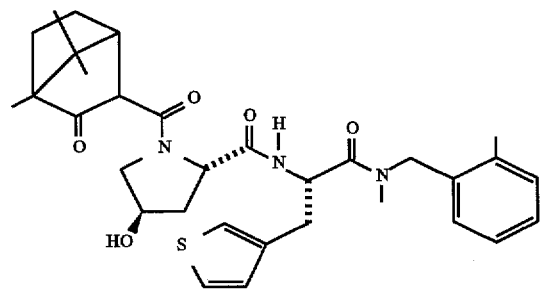
50
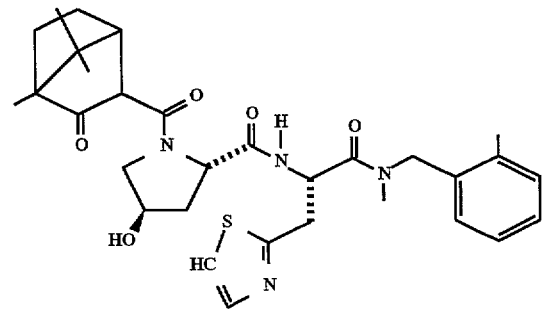
51
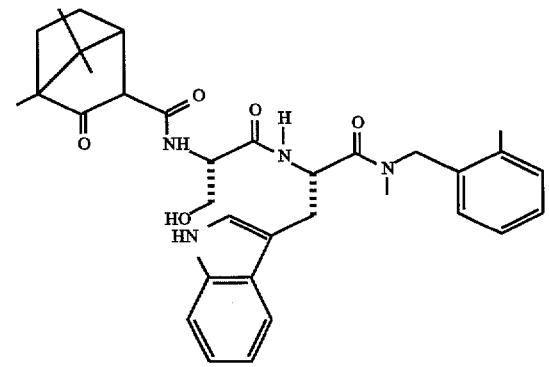
52

-continued
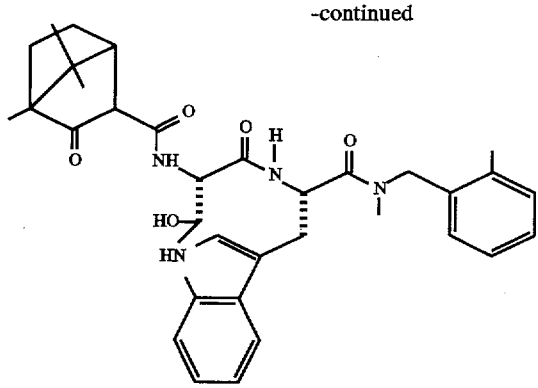
53
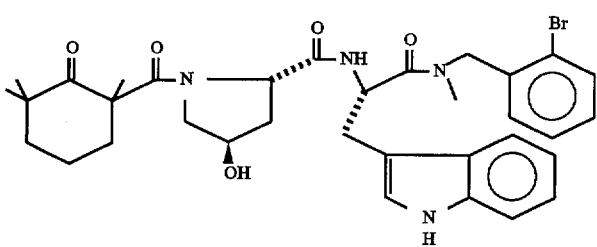
54
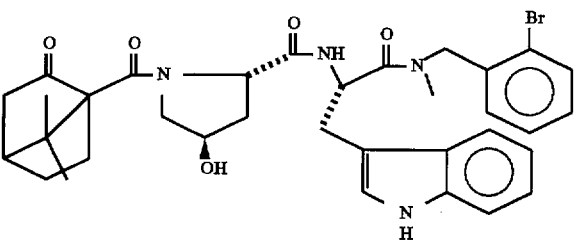
55
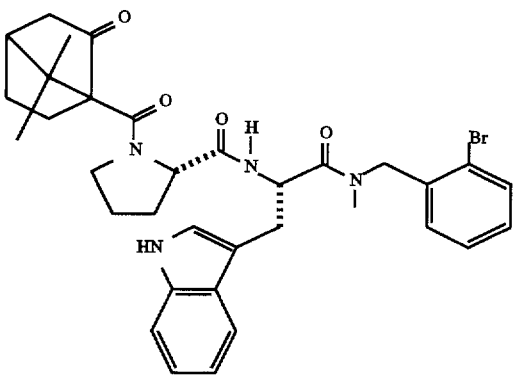
56
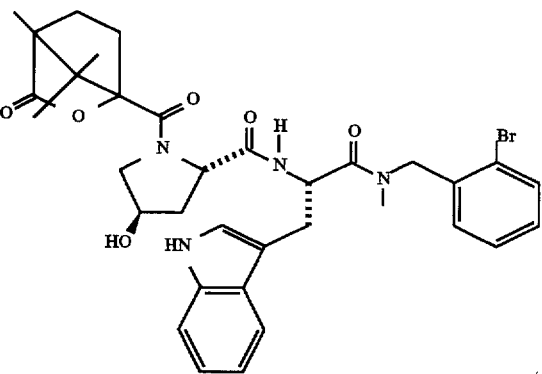
57

The compounds 56 and 57 contain groups $R^1$ (again in a simplified form of illustration), as do examples 55 and 24.

Of these compounds 1 to 5, 8, 15 to 18 and 43 are preferred.

In the illustration of the above formulae, the $CH_3$-groups are not given in full. Compound 1 contains, for example, the (+)-camphorcarboxylic acid group as group $R^1$—$R^{11}$.

The compounds according to the invention are valuable neurokinin (tachykinin)-antagonists which exhibit substance P-antagonism, but also have neurokinin A- and neurokinin-B antagonistic properties. They are useful for treating and preventing neurokinin-mediated diseases such as respiratory tract diseases e.g. asthma, bronchitis, rhinitis, cough or expectoration as well as inflammatory eye diseases such as conjunctivitis, inflammatory skin diseases such as dermatitis and urticaria, inflammatory intestinal diseases such as ulcerative colitis or Crohn's disease, other inflammatory diseases such as polyarthritis or osteoarthritis as well as painful conditions (for e.g. migraine) and gastro-intestinal complaints such as irritable colon and vomiting.

Of special interest to medicine are compounds whose $NK_1$- and $NK_2$- values are of a similar order of magnitude.

The invention, therefore, also relates to the use of the compounds according to the invention as drugs and pharmaceutical preparations containing these compounds. It is preferred if the compounds are used for human beings. They may be given intravenously, subcutaneously, intramuscularly, intraperitoneally, intranasally, inhalationally, transdermally, optionally assisted by iontophoresis or known enhancers, and orally.

For the parenteral administration, the compounds of formula I or the physiologically compatible salts thereof are placed in solution, suspension or emulsion, optionally with the substances normally used for this purpose such as solubilisers, emulsifiers or other excipients. The solubilisers used are for example: water, physiological sodium chloride solutions or alcohols such as ethanol, propanediol or glycerin, sugar solutions such as glucose or mannitol solutions or else a mixture of different solubilisers.

Furthermore, the compounds may be administered by implants, for example of polylactide, polyglycolide or polyhydroxybutyric acid or intranasal preparations.

The compounds may be prepared using generally known methods of amino and peptide chemistry, by condensing, step by step, the relevant amino acids or peptide derivative part sequences, carboxylic or sulphonic acids and amines and isolating the compound thus obtained in free form or in the form of the desired salt.

The dipeptide derivatives of formula Ia

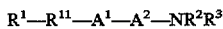
Ia may be synthesised from the parts $R^1$—$R^{11}OH$, H—$A^1$—OH, H—$A^2$—OH and $HN(R^3)R^2$, whereby the sequence of the couplings may be from right to left, from left to right or by coupling the units $R^1$—$R^{11}$—$A^1$—OH and H—$A^2$—N$(R^3)R^2$ (fragment couplings).

The compounds according to the invention may be prepared using generally known methods of peptide chemistry such as described in "Houben-Weyl, Methoden der organischen Chemie, Vol. 15/2", or using solid phase peptide synthesis (e.g. R. C. Sheppard, Int. J. Pept. Prot. Res., 21, 118 [1983]) or similar known methods. Here, the relevant amino acids or partial amino acid sequences are condensed step by step and the resultant peptides are isolated in free form or in the form of the desired salts. The amino protecting groups used are those described in "Houben-Weyl, Methoden der organischen Chemie, Vol. 15/1", whereby the benzyloxycarbonyl group (Z) is preferred in conventional syntheses and the fluorenylmethoxycarbonyl group (Fmoc) in solid phase syntheses. In the case of the conventional synthesis the side chain of the arginine was protected by protonation, in the case of the solid phase synthesis, the Mtr-group was used. In the solid phase peptide synthesis the following amino acids with protected side chains were, for example, used: Lys(Boc), His(Bum), Ser(tBu) and Asp(tBu). The specific synthesis conditions are apparent from the following Examples.

For the synthesis of the compounds of general formula I using the solid phase synthesis, those dipeptide carboxylic acids are initially synthesised which are reacted in solution to form dipeptide amides. The following anchor groups are suitable 1. Benzylester (G. Barang, R. B. Merrifield, Peptides 2, 1 (1980) Eds. E. Gross, J. Meienhofer, Academic Press, New York)

2. PAM-Anker (R. B. Merrifield, J. Am. Chem. Soc. 85, 2149 (1966))

3. Wang-Anker (S.-S. Wang, J. Am. Chem. Soc. 95, 1328 (1973))

4. SASRIN-Anker (M. Mergler, R. Tanner, J. Gostuli, P. Grogg, Tetrah. Lett. 29, 4005 (1988)).

For preparing the compounds of formula Ib

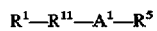
Ib the components $R^1$—$R^{11}OH$, the amino acid H—$A^1$—OH and the amine H—$R^5$ are bonded to one another. Optionally, the carboxylic acid of $R^1$—$R^{11}OH$ may first be coupled with a suitably protected form of H—$A^1$—OH and, following cleavage of the protecting group, condensed with the amine H—$R^5$, or the suitably protected amino acid H—$A^1$—OH may first be reacted with H—$R^5$ and this product may be coupled with $R^1$—$R^{11}OH$ after deprotection.

The basic forms of the amines H—$R^5$ may be obtained using known methods:

if H—$R^5$ is

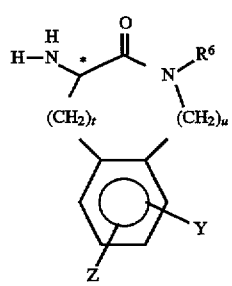
IIa with t=1 and u=0 and $R^6$, Y and Z are as hereinbefore described, the preparation is carried out using known methods as described by A. L. Davis et al., J. Med. Chem. 18, 752 (1975) or H. Merz, DE 38 23 576 (C.A. 114 (21), 207 052 m). The introduction of the group $R^6$ into a compound of general formula XI is carried out by reaction with NaH and BrR$^6$. This reaction may take place in the presence or absence of a protecting group (Sch) on the exocyclic N.

This preparation may be demonstrated by the following reaction scheme:

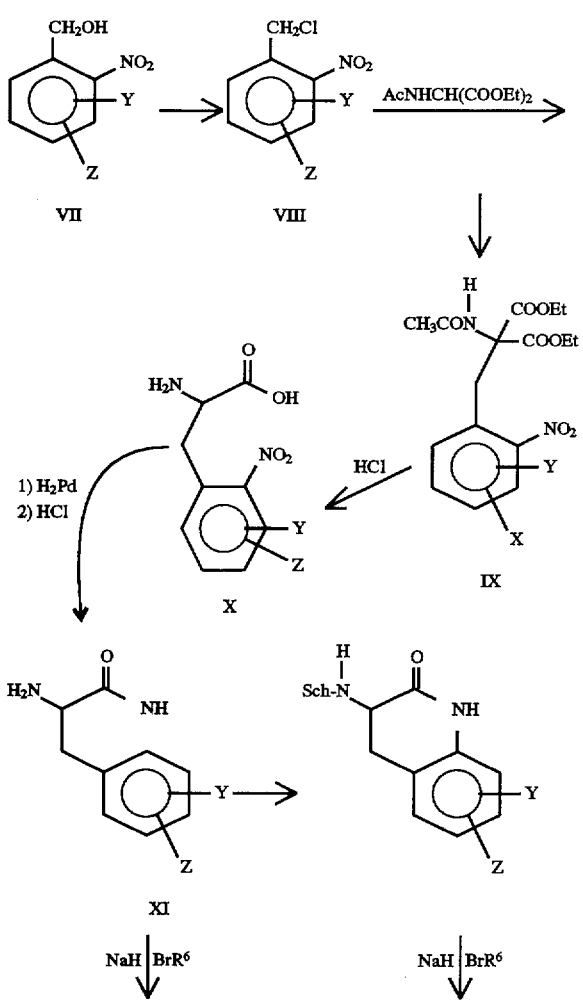

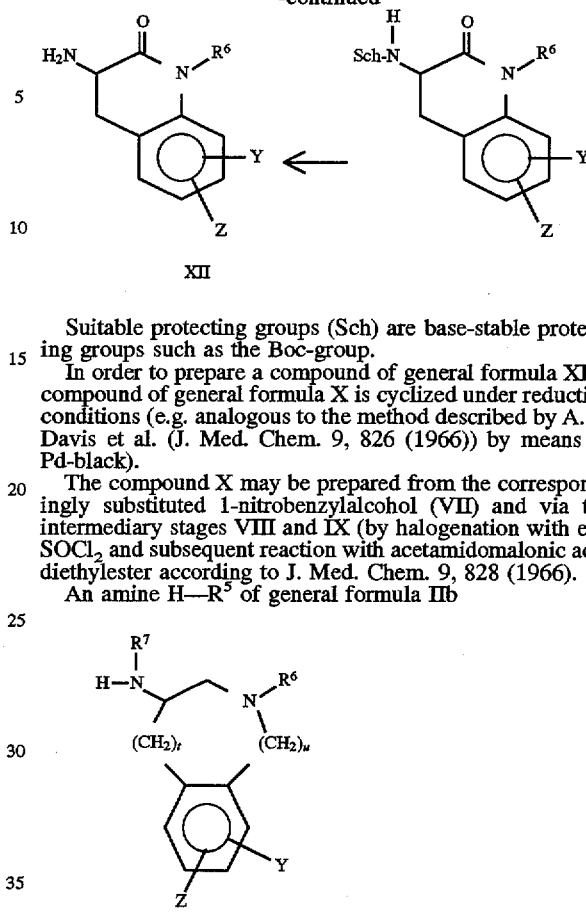

Suitable protecting groups (Sch) are base-stable protecting groups such as the Boc-group.

In order to prepare a compound of general formula XI, a compound of general formula X is cyclized under reductive conditions (e.g. analogous to the method described by A. L. Davis et al. (J. Med. Chem. 9, 826 (1966)) by means of Pd-black).

The compound X may be prepared from the correspondingly substituted 1-nitrobenzylalcohol (VII) and via the intermediary stages VIII and IX (by halogenation with e.g. $SOCl_2$ and subsequent reaction with acetamidomalonic acid diethylester according to J. Med. Chem. 9, 828 (1966).

An amine $H—R^5$ of general formula IIb

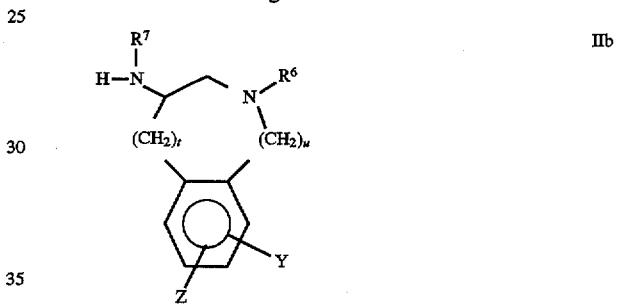

wherein t=1 and u=0 and $R^6$, Y and Z are as specified hereinbefore for formula IIa may be prepared by reduction of a corresponding compound IIa by means of e.g. $LiAlH_4$.

For preparing a compound IIa, wherein t=u=0 and $R^6$, Y and Z are as specified hereinbefore, the method according to A. L. Davis et al., J. Med. Chem. 16, 1043 (1973) is suitable. Here, starting from α-bromo-o-nitrophenylacetic acid methylester, the phthalimido group is introduced and after cleavage of the protecting groups and reduction of the nitro group, the cyclisation takes place to form (substituted or unsubstituted) 3-amino-2-indolinone:

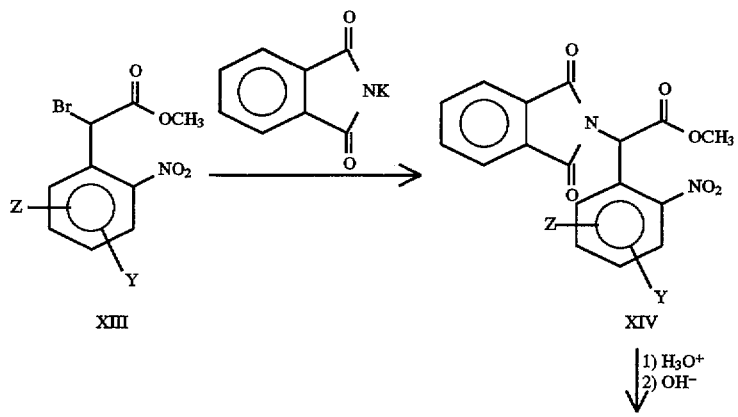

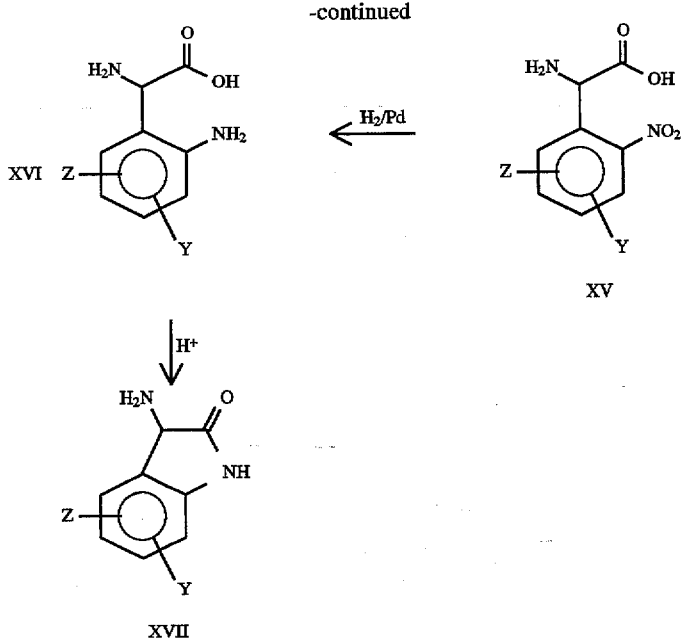

The introduction of $R^6$ and reduction to form the analogous compound of general formula IIb may be carried out as indicated above.

The preparation of compound IIa with t=2, u=0, wherein $R^6$, Y and Z is as defined above may be summarised by the following reaction scheme:

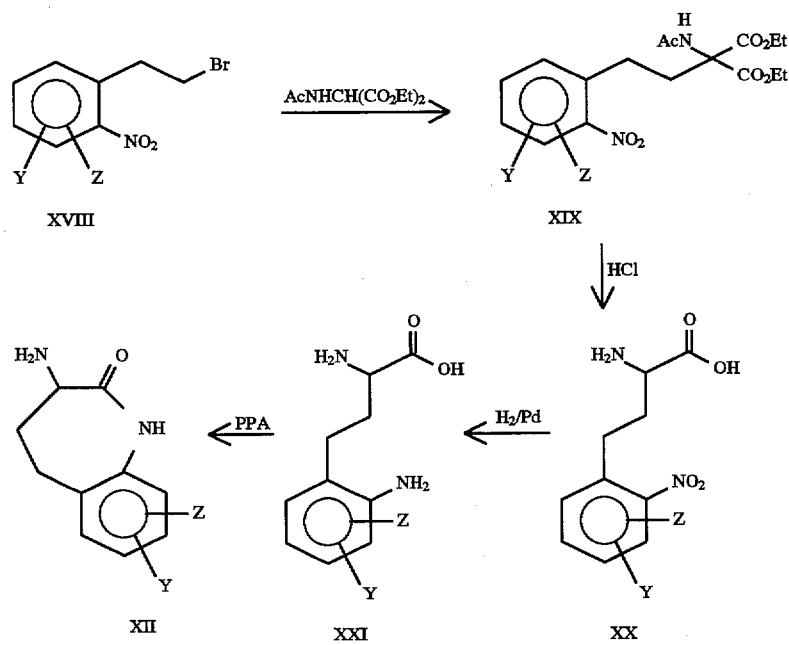

The introduction of $R^6$ and reduction to form the analogous compound IIb may be carried out as indicated above.

When using this preparation method, the correspondingly substituted 2-(2-nitrophenyl)-ethylbromide (XVIII) may be reacted with acetamidomalonic acid diethylester to form compound XIX and then XX, analogously to the methods described above.

The reduction of compound XX to form compound XXI may be carried out under pressure in a solution of MeOH and water, for example by hydrogen in the presence of Pd-black. The cyclisation to prepare compound XXII may be carried out with polyphosphoric acid whilst stirring and heating.

The preparation of compound IIa with t=u=1, wherein $R^6$, Y and Z are as defined above, may be carried out as follows:

unsubstituted or substituted phthaloylphenylalanine is coupled with the amine H$_2$N—R$^6$ and then cyclised with formaldehyde in a reaction of the Pictet-Spengler kind. Finally, the phthaloyl group is cleaved off, for example by treating with hydroxylamine:

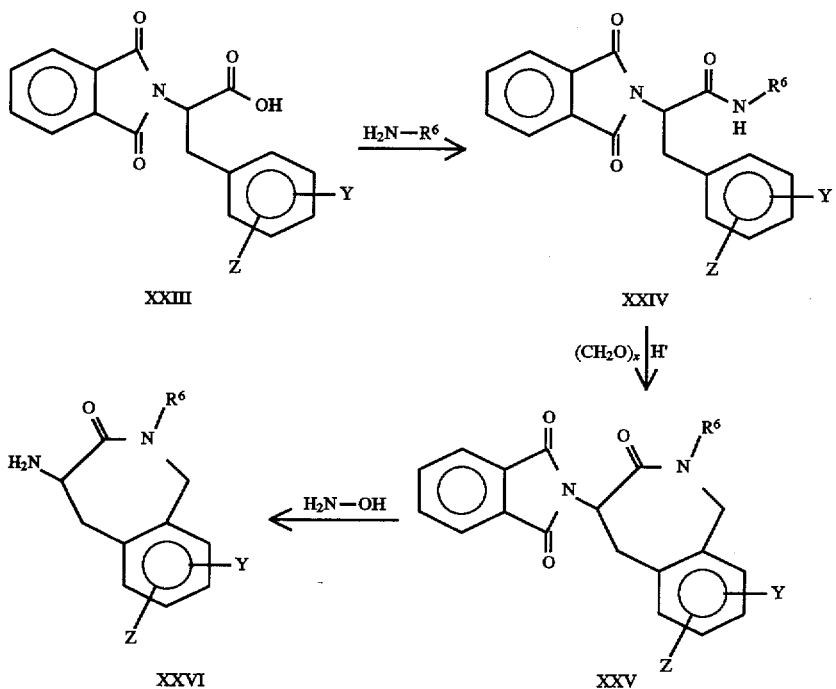

The reduction to form the analogous compound of general formula IIb may be carried out as indicated above.

The preparation of an amine HR$^5$ of general formula IIIa

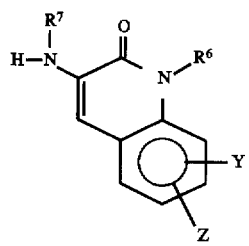

wherein R$^6$, Y and Z are as defined above may be carried out according to G-Leclerc et al., J. Med. Chem. 29, 2427 (1986). For this purpose, substituted or unsubstituted 3-bromoquinoline is first converted into the corresponding N-oxide, then transposed to the quinolin-2-one and finally the amino group is introduced with ammonia under pressure (in the carrier tube):

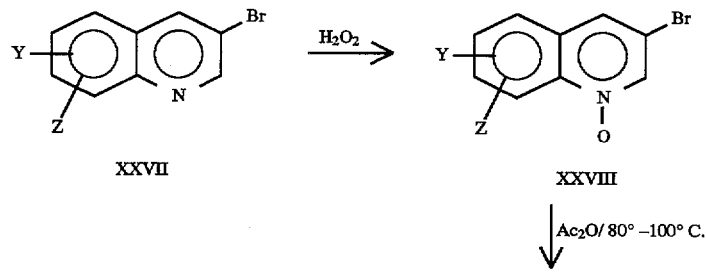

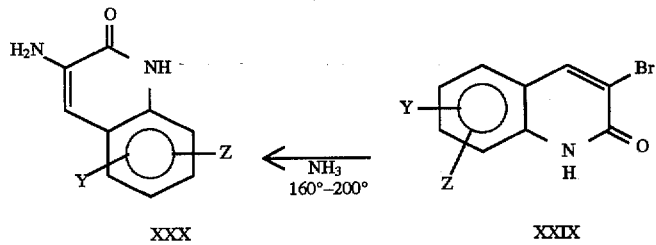

The introduction of the substituents $R^6$ may be carried out as described above with respect to compound IIa.

The preparation of a compound $HR^5$ of general formula IVa

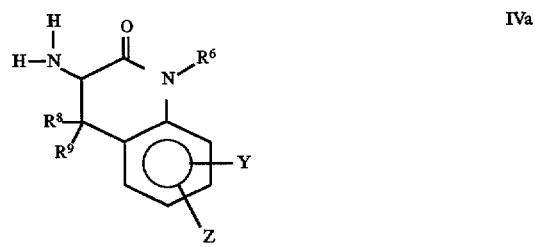

wherein $R^6$ is as defined above and $R^8$ represents hydroxy and $R^9$ is hydrogen, may be carried out according to R. Weichert, Arkiv Kemi 25, 231 (1966). Here, acetaminomalonic acid monoethylether is reacted with substituted or unsubstituted 2-nitrobenzaldehyde, then it is hydrolysed, the nitro group is reduced and finally the cyclisation is carried out:

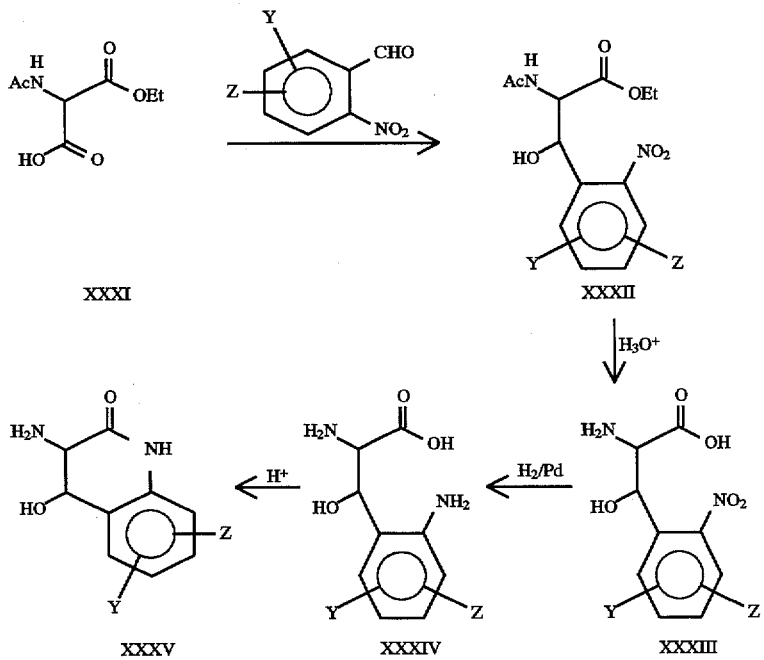

The introduction of R⁶ is carried out as described above.

In order to prepare a compound IVa wherein $R^9$ represents $(C_{1-5})$ alkoxy, phenyl-$(C_{1-5})$ alkyloxy, naphthyl-$(C_{1-5})$ alkyloxy or $(C_{1-4})$alkylcarbonyl or wherein $R^8$ and $R^9$ together represent oxygen or —$OCH_2CH_2O$—, the above compound IVa wherein $R^8$ represents hydrogen and $R^6$ represents hydroxy, may be reacted as follows:

a) for preparing a compound IVa, wherein $R^9$ is alkyloxy, phenyl or naphthylalkyloxy: etherication according to Williamson;

b) for preparing a compound IVa, wherein $R^9$ is alkylcarbonyl; reaction with the corresponding acid anhydride;

c) for preparing a compound IVa, wherein $R^8$ and $R^9$ together represent oxygen: oxidation according to e.g. Oppenauer;

d) for preparing a compound IVa, wherein $R^8$ and $R^9$ both represent —$OCH_2CH_2O$—: reaction of the keto compound obtained according to (c) with ethyleneglycol.

In order to prepare amines of general formula H—$R^5$, wherein $R^7$ is alkyl, the compounds of general formula IIa, IIb, IIIa and IVa are alkylated. This alkylation may be carried out by protecting the exocyclic N initially by e.g. trifluoroacetyl, carrying out the alkylation with e.g. alkyl-bromide and then cleaving the protecting group by e.g. hydrolysis.

Pharmaceutical Preparations:

| Pharmaceutical Preparations: |
|---|

Injection solution

| | | | |
|---|---|---|---|
| 200 | mg | active substance * | |
| 1.2 | mg | monopotassium dihydrogen phosphate = $KH_2PO_4$ | } (buffer) |
| 0.2 | mg | sodium dihydrogen phosphate = $NaH_2PO_4.2H_2O$ | |
| 94 | mg | sodium chloride | } (isotonic) |
| or | | | |
| 520 | mg | glucose | |
| 4 | mg | albumin | (protease protection) |
| q.s. | | sodium hydroxide solution | } to adjust the pH to pH 6 |
| q.s. | | hydrochloric acid | | sufficient water to make a 10 ml solution for injection purposes

Injection solution

| | | |
|---|---|---|
| 200 | mg | active substance* |
| 94 | mg | sodium chloride |
| or | | |
| 520 | mg | glucose |
| 4 | mg | albumin |
| q.s. | | sodium hydroxide solution } to adjust the pH to pH 9 |
| q.s. | | hydrochloric acid | sufficient water to make a 10 ml solution for injection purposes

Lyophilisate

| | | |
|---|---|---|
| 200 | mg | active substance* |
| 520 | mg | mannitol (isotonic/structure builder) |
| 4 | mg | albumin |

Solvent 1 for lyophilisate
  10 ml water for injection purposes
Solvent 2 for lyophilisate
  20 mg Polysorbat ®80 = Tween ®80 (surface-active substance)
  10 ml water for injection purposes

*Active substance: compounds according to the invention, for example the compound of Example 1 or 201.
Dosage for human beings of 67 kg: 1 to 500 mg

EXAMPLE 1 tert.-Butyloxycarbonyl-(2S)-2-naphthylalanyl-(2-methoxyphenyl)piperazide (I)

3.15 g of tert.-Butyloxycarbonyl-L-2-naphthylalanine and 1.8 g of N,N'-Carbonyldiimidazole were stirred in 100 ml of THF for 2.5 hours. 1.93 g of 1-(2-Methoxyphenyl) piperazine were added, stirred for 12 hours at ambient temperature and then the THF was distilled off in vacuo. Then the mixture was taken up in 100 ml of ethyl acetate, extracted with 10% $KHCO_3$-solution and water, the ethyl acetate phase was dried over $Na_2SO_4$ and concentrated in vacuo.

4.9 g of colourless oil tert.-Butyloxycarbonyl-(2S,4R)-4-hydroxyprolyl-(2S)-2-naphthylalanyl-(2-methoxyphenyl)-piperazide(II)

4.9 g of I were stirred in 50 ml of trifluoracetic acid/dichlormethane (1:1) for 45 minutes at ambient temperature, the solution was concentrated by evaporation in vacuo, the residue was dissolved in ethyl acetate and extracted twice with 10% $KHCO_3$ solution and twice with water, the ethyl acetate phase was dried and concentrated by evaporation. The oily residue was dissolved in 50 ml of DMF/Dichloromethane (1:1) and mixed with 2.3 g of tert.-Butyloxycarbonyl (2S,4R)-4-hydroxyproline, 1.6 g of 1-Hydroxybenzotriazole, adjusted to pH 9.5 with 3 ml of Diisopropylethylamine, and then 3.8 g of Tetramethyluronium tetrafluoroborate were added and the mixture was stirred for 24 hours. The solution was concentrated by evaporation in high vacuum, the residue was taken up in ethyl acetate and extracted twice with 10% $KHCO_3$ solution and twice with saturated NaCl-solution, dried and concentrated by evaporation.

5.4 g of yellow oil (90% of theory).

(+)-Camphor-3-carbonyl-(2S,4R)-4-hydroxypropyl (2S )-2-naphthylalanyl-(2-methoxyphenyl) piperazide (1)

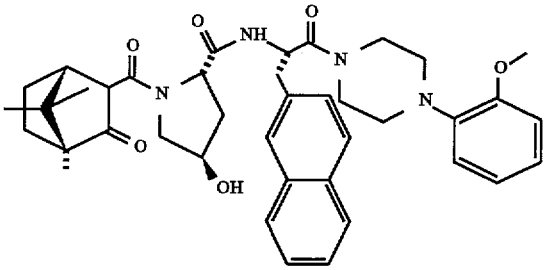

0.6 g of II were stirred with 20 ml of Trifluoracetic acid/Dichloromethane (1:1) for 45 minutes at ambient temperature, concentrated by evaporation and taken up in ethyl acetate, extracted with 10% $KHCO_3$-solution and water, dried and concentrated by evaporation. The residue was taken up in 40 ml of DMF/Dichloromethane (1:1), mixed with 0.2 g (+)-Camphor-3-carboxylic acid, 0.16 g of 1-Hydroxybenzotriazole, 1 ml of Diisopropylethylamine and 0.38 g of Tetramethyluronium tetrafluoroborate and stirred for 12 hours at ambient temperature. After concentration, the mixture is taken up in ethyl acetate, extracted twice with 10% $KHCO_3$ solution and twice with water, dried and concentrated by evaporation. The hydrochloride salt is precipitated by the addition of ethereal HCl.

310 mg (45 % of theory).

EXAMPLE 2

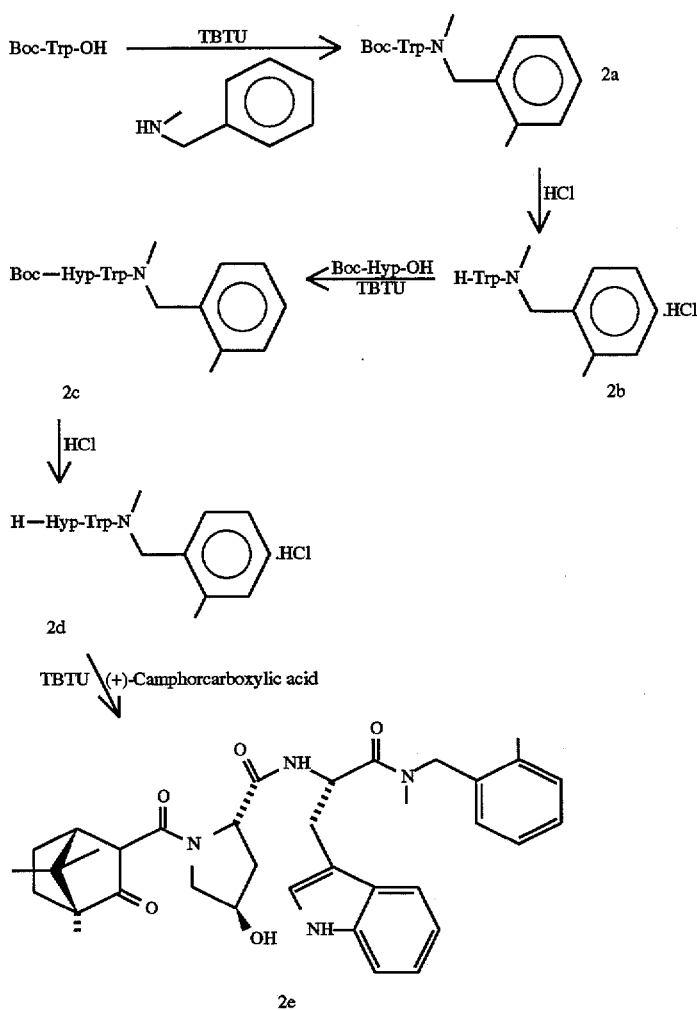

EXAMPLE 2

Preparation of 2a:

7.0 g of Boc-L-Tryptophan (23 mMol) and 3.1 g of N-Methyl-(o-methylbenzyl)-amine (23 mM) were dissolved in 200 ml of DMF, mixed with 7.75 g of TBTU (24 mM) and adjusted to about pH 8 by adding a few drops of Triethylamine. After 24 hours at ambient temperature, the mixture was concentrated to dryness in vacuo, the residue was taken up in 300 ml of ethyl acetate, extracted 3 times with 150 ml of 0.5n HCl each and 3 times with 150 ml of NaHCO$_3$ solution each. The ethyl acetate phase was dried with MgSO$_4$, filtered and concentrated to dryness, yielding 7.4 g of 2a as an ivory-coloured solid substance. M.p.: 70°–84° C.

$[\alpha]_D^{20}$=34.3° (MeOH)

Preparation of 2b:

6.8 g of 2a (16 mM) were mixed with 200 ml of 4n HCl in Dioxane and stirred for 1 hour at ambient temperature. The reaction solution was concentrated to dryness, the residue was stirred with ether, suctioned off, washed with ether and dried in a desiccator. 6.47 g of hydrochloride 2b were obtained as a pink powder.

Preparation of 2c:

4.5 g of 2b (12.6 mM) and 2.91 g of Boc-(2S,4R)-Hydroxyproline were dissolved in 120 ml of DMF, mixed with 4.3 g of TBTU (13.4 mM) and adjusted to a pH value of about 8 by adding TEA. After 24 hours of stirring at ambient temperature, the mixture was concentrated to dryness, taken up in 400 ml of ethyl acetate, extracted 3 x with 200 ml of 0.5n HCl and 3 times with 200 ml of 1n NaHCO$_3$ solution each, and the organic phase was dried over MgSO$_4$ filtered and concentrated by evaporation. 6.33 g of 2c were obtained as a cream coloured solid substance.

Preparation of 2d:

The Boc-protecting group was cleaved in the way as described under Preparation of 2b. Here, 4.7 g of the hydrochloride 2d was obtained as a cream-coloured powder.

Preparation of 2e:

1.2 g of 2d (2,55 mM) and 0.5 g of (+)-Camphorcarboxylic acid (2.55 mM) were combined with 30 ml of CH$_2$Cl$_2$ and 0.9 g of TBTU (2,8 mM), adjusted to pH 8 by adding TEA and stirred for 24 hours at ambient temperature. The reaction mixture was concentrated to dryness and the residue was chromatographed over silica gel using CH$_2$Cl$_2$/MeOH=9:1 as eluent. The combined fractions were concentrated yielding 0.49 g of 2e as a cream-coloured solid substance:

M.p.: 55°–64° C.

$[\alpha]_D^{20}$=–21.4° (MeOH)

EXAMPLE 3

(Compound 34)

Compound 2d TBTU (−)-Camphorcarboxylic acid

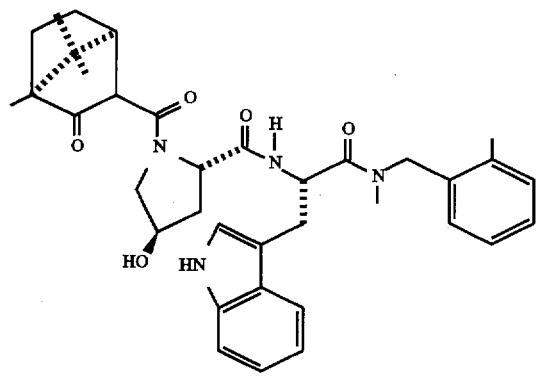

The synthesis of 2d was carried out as in Example 2. 0.63 g of 2d (1.34 mMol) and 0.26 g (−)-Camphorcarboxylic acid were dissolved in 25 ml of DMF, the pH value was adjusted to 8 by adding 0.38 ml of TEA, and 0.48 g of TBTU were added. The preparation mixture was stirred overnight at ambient temperature and then concentrated to dryness on the rotary evaporator. The residue was dissolved in ethyl acetate and chromatographed over silica gel with ethyl acetate as mobile solvent. Here, the above compound was obtained as a white solid substance. Yield: 0.46 g.

M.p.: 125°–144° C.; $[\alpha]_D^{20} = -81.9°$ (MeOH)

The other compounds of this invention may be prepared analogously, for example the above mentioned compounds 1 to 53.

List of the physical data of Compounds 1 to 56.

| Compound | Mp [°C.] | |
|---|---|---|
| 1 | 159–164 | |
| 2 | 55–64 | |
| 3 | 138–148 | |
| 4 | 148–152 | |
| 5 | 160–170 | decomposition |
| 6 | 178–184 | |
| 7 | 140–145 | |
| 8 | 145–155 | |
| 9 | 245–250 | |
| 10 | 182–186 | |
| 11 | 120–128 | |
| 12 | 165–176 | decomposition |
| 13 | 175–180 | |
| 14 | 200–215 | |
| 15 | 140–144 | decomposition |
| 16 | 141–145 | |
| 17 | 155–160 | |
| 18 | 160–165 | |
| 19 | 130–135 | decomposition |
| 20 | 143–147 | decomposition |
| 21 | 163–167 | |
| 22 | 194–197 | |
| 23 | 125–129 | decomposition |
| 24 | 140–148 | |
| 25 | solid oil | |
| 26 | 138–146 | |
| 27 | 72–76 | |
| 28 | 132–138 | |
| 34 | 125–144 | |
| 42 | 139–143 | |
| 43 | 124 | |
| 44 | 134–136 | |
| 45 | 111–118 | |
| 46 | 120–142 | |

-continued

| Compound | Mp [°C.] |
|---|---|
| 47 | 120–140 |
| 48 | 108–110 |
| 55 | 132–136 |
| 56 | 118–123 |

What is claimed is:

1. An amino acid derivative of formula I:

$$R^1-R^{11}-A^1-B$$

or the pharmaceutically acceptable salts thereof, wherein $R^1$ is selected from the group consisting of

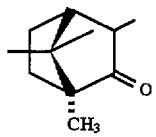

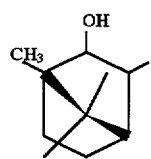

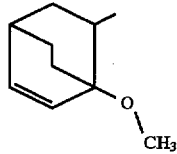

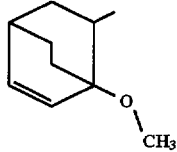

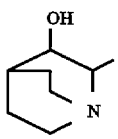

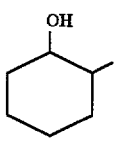

-continued

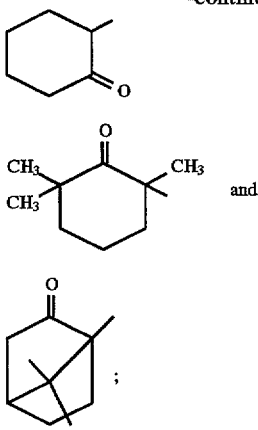

$R^{11}$ is —C(O)—;

$A^1$ is selected from the group consisting of a proline radical and a 4-hydroxyproline radical wherein the proline or hydroxyproline radical is attached to $R^{11}$ by way of the ring nitrogen and is attached to B by way of side chain carbonyl;

B is the group —$A^2$—$NR^2R^3$;

$A^2$ is selected from the group consisting of

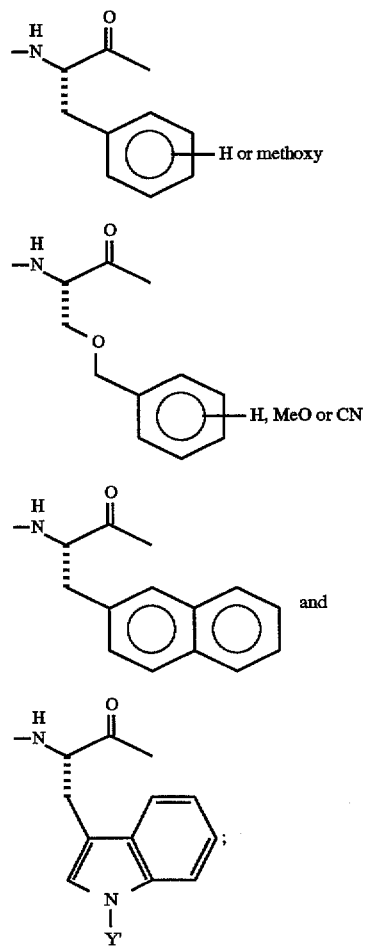

Y' is selected from the group consisting of H and $CH_3$;

$R^2$ and $R^3$ are independently selected from the group consisting of alkyl, arylalkyl, heteroaryl and hydroxy (wherein aryl is selected from the group consisting of phenyl; mono-, di- or tri-substituted phenyl; and naphthyl, wherein the phenyl substituents are independently selected from the group consisting of halogen, trihalomethyl, alkoxy, alkyl, alkylthio, hydroxy, nitro, trifluoromethoxy, dialkylamino and cyano, or two adjacent positions of the phenyl group are linked by —O—$(CH_2)_{1\,or\,2}$—O—; heteroaryl is selected from the group consisting of indolyl, pyridyl, pyrrolyl, imidazolyl and thienyl; and the alkyl and alkoxy groups have from one to three carbon atoms).

2. The amino acid derivative according to claim 1, wherein $R^2$ and $R^3$ are independently selected from the group consisting of alkyl, arylalkyl, heteroaryl and hydroxy (wherein aryl is selected from the group consisting of phenyl; mono-, di- or tri-substituted phenyl; or naphthyl, wherein the phenyl substituents are independently selected from the group consisting of halogen, trihalomethyl, alkoxy, alkyl and cyano; heteroaryl is selected from the group consisting of indolyl, pyridyl, pyrrolyl, imidazolyl and thienyl; and the alkyl and alkoxy groups have from one to three carbon atoms).

3. The amino acid derivative according to claims 1 or 2, wherein $R^1$ is

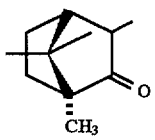

4. The amino acid derivative according to claim 1, wherein $A^1$ is a 4-hydroxyproline radical with 2-S configuration.

5. The amino acid derivative according to claim 1, wherein $A^2$ is in the S-configuration.

6. The amino acid derivative according to claim 5, wherein $A^2$ is selected from the group consisting of

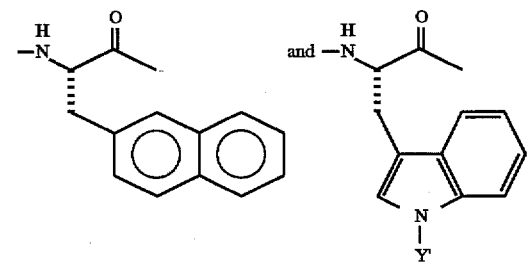
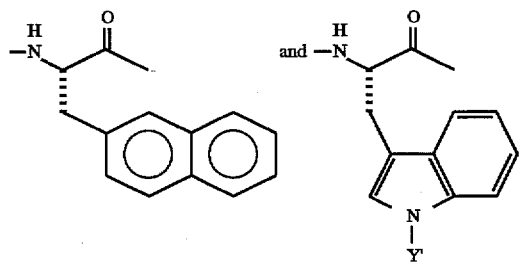

and Y' is selected from the group consisting of H and methyl.

7. The amino acid derivative according to claim 6, wherein $A^2$ is

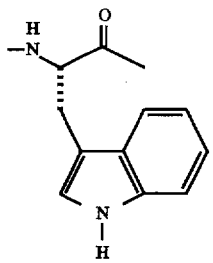

8. The amino acid derivative according to claim 1, wherein $R^2$ is alkyl and $R^3$ is arylalkyl (wherein aryl is selected from the group consisting of phenyl and mono-, di- or tri-substituted phenyl; wherein the phenyl substituents are independently selected from the group consisting of halogen, trihalomethyl, alkoxy, alkyl and cyano; heteroaryl is selected from the group consisting of indolyl, pyridyl, pyrrolyl, imidazolyl and thienyl; and the alkyl and alkoxy groups have from one to three carbon atoms).

9. The amino acid derivative according to claim 8, wherein the substituent on the phenyl is in the 2-position.

10. The amino acid derivative according to claim 8, wherein $R^3$ is unsubstituted benzyl or benzyl monosubstituted with halogen or alkyl.

11. The amino acid derivative according to claim 10, wherein $R^2$ is methyl and $R^3$ is 2-methylbenzyl.

12. An amino acid derivative having the formula:

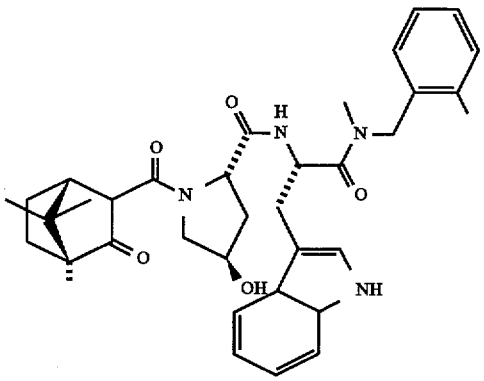

13. A pharmaceutical composition comprising the amino acid derivative according to any one of claims 1–12 and a pharmaceutically acceptable carrier.

* * * * *